(12) United States Patent
Helenek et al.

(10) Patent No.: US 10,478,450 B2
(45) Date of Patent: *Nov. 19, 2019

(54) METHODS AND COMPOSITIONS FOR ADMINISTRATION OF IRON

(71) Applicant: Luitpold Pharmaceuticals, Inc., Shirley, NY (US)

(72) Inventors: Mary Jane Helenek, Brookville, NY (US); Marc L. Tokars, Douglassville, PA (US); Richard P. Lawrence, Calverton, NY (US)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/683,415

(22) Filed: Apr. 10, 2015

(65) Prior Publication Data

US 2015/0297630 A1     Oct. 22, 2015

Related U.S. Application Data

(63) Continuation of application No. 13/847,254, filed on Mar. 19, 2013, now abandoned, which is a continuation of application No. 12/787,283, filed on May 25, 2010, now Pat. No. 8,431,549, which is a continuation of application No. 11/620,986, filed on Jan. 8, 2007, now Pat. No. 7,754,702.

(60) Provisional application No. 60/757,119, filed on Jan. 6, 2006.

(51) Int. Cl.
| | |
|---|---|
| *A61K 31/7135* | (2006.01) |
| *A61K 31/715* | (2006.01) |
| *A61K 31/721* | (2006.01) |
| *C07H 23/00* | (2006.01) |

(52) U.S. Cl.
CPC ........ *A61K 31/7135* (2013.01); *A61K 31/715* (2013.01); *A61K 31/721* (2013.01); *C07H 23/00* (2013.01)

(58) Field of Classification Search
CPC .......................... A61K 31/7135; A61K 31/715
See application file for complete search history.

(56) References Cited

U.S. PATENT DOCUMENTS

| | | | |
|---|---|---|---|
| 2,807,610 A | 9/1957 | Zief et al. | |
| 3,076,798 A | 2/1963 | Mueller et al. | |
| 3,100,202 A | 8/1963 | Muller et al. | |
| 3,639,588 A | 2/1972 | Alsop et al. | 424/180 |
| 4,599,405 A | 7/1986 | Muller et al. | 536/113 |
| 5,541,158 A | 7/1996 | Vance et al. | |
| 5,624,668 A | 4/1997 | Lawrence et al. | |
| 6,219,440 B1 | 9/2001 | Andreasen et al. | 514/59 |
| 6,599,498 B1 | 7/2003 | Groman et al. | |
| 6,960,571 B2 | 11/2005 | Helenek et al. | |
| 6,977,249 B1 | 12/2005 | Andreasen et al. | 514/59 |
| 7,612,109 B2 | 11/2009 | Geisser et al. | |
| 7,754,702 B2 | 7/2010 | Helenek et al. | 514/54 |
| 7,871,597 B2 | 1/2011 | Groman et al. | |
| 8,431,549 B2 | 4/2013 | Helenek et al. | 514/58 |
| 8,815,301 B2 | 8/2014 | Andreasen | 424/647 |
| 8,895,612 B2 | 11/2014 | Helenek et al. | 512/502 |
| 9,439,969 B2 | 9/2016 | Andreasen | 536/112 |
| 2003/0232084 A1 | 12/2003 | Groman et al. | |
| 2004/0180849 A1 | 9/2004 | Helenek et al. | |
| 2006/0116349 A1 | 6/2006 | Helenek et al. | 514/54 |
| 2006/0205691 A1 | 9/2006 | Geisser et al. | 514/59 |
| 2007/0161600 A1 | 7/2007 | Helenek et al. | 514/54 |
| 2008/0234226 A1 | 9/2008 | Erichsen et al. | 514/59 |
| 2014/0121193 A1 | 5/2014 | Katz et al. | 514/210.16 |
| 2014/0364598 A1 | 12/2014 | Andreasen | 536/112 |
| 2015/0320031 A1 | 11/2015 | Andreasen | 435/1.3 |
| 2016/0333118 A1 | 11/2016 | Andreasen | 536/112 |

FOREIGN PATENT DOCUMENTS

| | | |
|---|---|---|
| CA | 623411 | 7/1961 |
| CA | 2493806 | 5/2004 |
| CN | 101365458 | 2/2009 |
| KR | 10-2005-0070014 | 7/2005 |
| WO | WO 1997/011711 | 4/1997 |
| WO | WO 2002/46241 | 6/2002 |
| WO | WO 2004/037865 | 5/2004 |
| WO | WO 2007/023154 | 3/2007 |
| WO | WO2007081744 | 7/2007 |
| WO | WO 2014/058516 | 4/2014 |

OTHER PUBLICATIONS

Cook, J.D., (Best Practice & Research Clinical Haematology, 2005, 18(2), p. 319-332, Available online Feb. 25, 2005.*

Lyseng-Williamson et al., Ferric Carboxymaltose—A Review of its Use in Iron-Deficiency Anaemia, Drugs, Apr. 2009, vol. 69, Issue 6, pp. 739-756.

van Zyl-Smit R. et al., Experience with the Use of an Iron Polymaltose (Dextrin) Complex Given by Single Total Dose Infusion to Stable Chronic Haemodialysis Patients, Nephron, 2002, vol. 92, pp. 316-323.

Letter/Written Disclosure of the initial Information Disclosure Statement for the above-referenced application, filed herewith on Jan. 27, 2 pages.

Auerbach et al., "Low-molecular weight iron dextran and iron sucrose have similar comparative safety profiles in chronic kidney disease," Kidney International 73:528-530 (2008).

(Continued)

*Primary Examiner* — Eric Olson
(74) *Attorney, Agent, or Firm* — Dentons US LLP; Stephanie Seidman

(57) ABSTRACT

The present invention generally relates to treatment of iron-related conditions with iron carbohydrate complexes. One aspect of the invention is a method of treatment of iron-related conditions with a single unit dosage of at least about 0.6 grams of elemental iron via an iron carbohydrate complex. The method generally employs iron carbohydrate complexes with nearly neutral pH, physiological osmolarity, and stable and non-immunogenic carbohydrate components so as to rapidly administer high single unit doses of iron intravenously to patients in need thereof.

22 Claims, 2 Drawing Sheets

(56) References Cited

OTHER PUBLICATIONS

Danielson B.G., "Structure, chemistry, and pharmacokinetics of intravenous iron agents," J Am Soc Nephrol 15 Suppl 2:S93-S98 (2004).
Decision of the Technical Board of Appeal, dated Mar. 1, 2006, in connection with European Patent No. 0679508, 17 pages.
Fisons Pharmaceuticals, "Imferon," US drug monograph, 2 pages (1989).
Jahn et al., "A comparative study of the physiochemical properties of iron isomaltoside 1000 (Monofer), a new intravenous iron preparation and its clinical implications," European J of Pharmaceutics and Biopharmaceutics 78:480-491 (2011).
Johansson et al., "Intravenous iron isomaltoside 1000 (Monofer®) reduces postoperative anaemia in preoperatively non-anaemic patients undergoing elective or subacute coronary artery bypass graft, valve replacement or a combination thereof: a randomized double-blind placebo-controlled clinical trial (the PROTECT trial)," Vox Sang 109(3):257-266 (2015).
Kulnigg et al., "A novel intravenous iron formulation for treatment of anemia in inflammatory bowel disease: the ferric carboxymaltose (FERINJECT) randomized controlled trial," Am J Gastroenterol 103(5): 1182-1192 (2008).
MacDougall et al., "Use of intravenous iron supplementation in chronic kidney disease" Iranian J Kidney Dis 7(1):9-22 (2013).
MacDougall I.C., "Strategies for iron supplementation: Oral versus intravenous" Kidney International 55(69): S61-66 (1999).
Reinisch et al., "A randomized, open-label, non-inferiority study of intravenous iron isomaltoside 1,000 (Monofer) compared with oral iron for treatment of anemia in IBD (PROCEED)," Am J Gastroenterol 108(12):1877-88 (2013).
Reinisch et al., "A 1-year trial of repeated high-dose intravenous iron isomaltoside 1000 to maintain stable hemoglobin levels in inflammatory bowel disease," Scand J Gastroenterol 50(10):1226-1233 (2015).
Syner-Med, "Summary of Product Characteristics; Ferinject," (2009), 8 pages.
Office Action, dated Dec. 15, 2009, in connection with U.S. Appl. No. 11/620,986, 21 pages.
Response, dated Jan. 8, 2010, in connection with U.S. Appl. No. 11/620,986, 13 pages.
Notice of Allowance, dated Apr. 5, 2010, in connection with U.S. Appl. No. 11/620,986, 12 pages.
Petition for Inter Partes Review of U.S. Pat. No. 7,754,702, dated Jun. 24, 2015, in connection with U.S. Appl. No. 11/620,986, 65 pages.
Patent Owner Preliminary Response, dated Oct. 12, 2015, in connection with U.S. Appl. No. 11/620,986 (U.S. Pat. No. 7,754,702), 39 pages.
Decision, dated Jan. 8, 2016, in connection with U.S. Appl. No. 11/620,986 (U.S. Pat. No. 7,754,702), 20 pages.
Order Conduct of the Proceedings, dated Mar. 11, 2016, in connection with U.S. Appl. No. 11/620,986 (U.S. Pat. No. 7,754,702), 6 pages.
Patent Owner Response, dated Mar. 29, 2016, in connection with U.S. Appl. No. 11/620,986 (U.S. Pat. No. 7,754,702), 47 pages.
Patent Owner Exhibit List as of Mar. 29, 2016, dated Mar. 29, 2016, in connection with U.S. Appl. No. 11/620,986 (U.S. Pat. No. 7,754,702), 7 pages.
Motion to Amend, dated Mar. 29, 2016, in connection with U.S. Appl. No. 11/620,986 (U.S. Pat. No. 7,754,702), 48 pages.
Petitioner's Notice of Objections to Evidence, dated Apr. 5, 2016, in connection with U.S. Appl. No. 11/620,986 (U.S. Pat. No. 7,754,702), 5 pages.
Corrected Patent Owner Exhibit List as of Apr. 25, 2016, dated Apr. 25, 2016, in connection with U.S. Appl. No. 11/620,986 (U.S. Pat. No. 7,754,702),7 pages.
Corrected Motion to Amend, dated Apr. 25, 2016, in connection with U.S. Appl. No. 11/620,986 (U.S. Pat. No. 7,754,702), 48 pages.

Petitioner's Reply to Patent Owner Response, dated Jun. 20, 2016, in connection with U.S. Appl. No. 11/620,986 (U.S. Pat. No. 7,754,702), 32 pages.
Petitioner's Opposition to Patent Owner's Motion to Amend, dated Jun. 20, 2016, in connection with U.S. Appl. No. 11/620,986 (U.S. Pat. No. 7,754,702), 31 pages.
Objections to Petitioner's Reply and Opposition Evidence, dated Jun. 27, 2016, in connection with U.S. Appl. No. 11/620,986 (U.S. Pat. No. 7,754,702), 5 pages.
Patent Owner Reply to Opposition to Motion to Amend, dated Jul. 19, 2016, in connection with U.S. Appl. No. 11/620,986 (U.S. Pat. No. 7,754,702), 20 pages.
Patent Owner Motion to Exclude, dated Aug. 9, 2016, in connection with U.S. Appl. No. 11/620,986 (U.S. Pat. No. 7,754,702), 19 pages.
Order Conduct of the Proceedings, dated Aug. 19, 2016, in connection with U.S. Appl. No. 11/620,986 (U.S. Pat. No. 7,754,702), 3 pages.
Order Trial Hearing, dated Aug. 22, 2016, in connection with U.S. Appl. No. 11/620,986 (U.S. Pat. No. 7,754,702), 5 pages.
Petitioner's Opposition to Patent Owner's Motion to Exclude, dated Aug. 23, 2016, in connection with U.S. Appl. No. 11/620,986 (U.S. Pat. No. 7,754,702), 19 pages.
Patent Owner Reply to Opposition to Motion to Exclude, dated Aug. 30, 2016, in connection with U.S. Appl. No. 11/620,986 (U.S. Pat. No. 7,754,702), 9 pages.
Record of Oral Hearing, dated Nov. 3, 2016, in connection with U.S. Appl. No. 11/620,986 (U.S. Pat. No. 7,754,702), 104 pages.
Final Written Decision, dated Jan. 4, 2017, in connection with U.S. Appl. No. 11/620,986 (U.S. Pat. No. 7,754,702), 52 pages.
Restriction Requirement, dated Mar. 23, 2012, in connection with U.S. Appl. No. 12/787,283, 7 pages.
Response, dated Apr. 19, 2012, to Restriction Requirement, dated Mar. 23, 2012, in connection with U.S. Appl. No. 12/787,283, 4 pages.
Office Action, dated Jun. 6, 2012, in connection with U.S. Appl. No. 12/787,283, 13 pages.
Response, dated Dec. 6, 2012, to Office Action, dated Jun. 6, 2012, in connection with U.S. Appl. No. 12/787,283, 34 pages.
Applicant-Initiated Interview Summary, dated Feb. 6, 2013, in connection with U.S. Appl. No. 12/787,283, 4 pages.
Notice of Allowance, dated Feb. 28, 2013, in connection with U.S. Appl. No. 12/787,283, 14 pages.
Petition for Inter Partes Review of U.S. Pat. No. 8,431,549, dated Jun. 24, 2015, in connection with U.S. Appl. No. 12/787,283, 67 pages.
Patent Owner Preliminary Response, dated Oct. 12, 2015, in connection with U.S. Appl. No. 12/787,283 (U.S. Pat. No. 8,431,549), 65 pages.
Order Conduct of the Proceeding, dated Oct. 14, 2015, in connection with U.S. Appl. No. 12/787,283 (U.S. Pat. No. 8,431,549), 4 pages.
Notice of Response in lieu of Motion, dated Oct. 20, 2015, in connection with U.S. Appl. No. 12/787,283 (U.S. Patent No. 431,549), 4 pages.
Petitioner's Objection to Patent Owner Response in Lieu of Motion, dated Oct. 30, 2015, in connection with U.S. Appl. No. 12/787,283 (U.S. Pat. No. 8,431,549), 4 pages.
Inter Partes Review Decision, dated Jan. 8, 2016, in connection with U.S. Appl. No. 12/787,283 (U.S. Pat. No. 8,431,549), 24 pages.
Request for Rehearing, dated Jan. 22, 2016, in connection with U.S. Appl. No. 12/787,283 (U.S. Pat. No. 8,431,549), 8 pages.
Patent Owner Objections to Evidence, dated Jan. 27, 2016, in connection with U.S. Appl. No. 12/787,283 (U.S. Pat. No. 8,431,549), 4 pages.
Revised Patent Owner Notice of Deposition of Dr. Linhardt, dated Feb. 19, 2016, in connection with U.S. Appl. No. 12/787,283 (U.S. Pat. No. 8,431,549), 3 pages.
Decision Denying Petitioner's Request for Rehearing, dated Feb. 26, 2016, in connection with U.S. Appl. No. 12/787,283 (U.S. Pat. No. 8,431,549), 5 pages.
Order re Conference Call on Mar. 9, 2016, dated Mar. 11, 2016, in connection with U.S. Appl. No. 12/787,283 (U.S. Pat. No. 8,431,549), 6 pages.

(56) References Cited

OTHER PUBLICATIONS

Patent Owner Exhibit List dated Jul. 19, 2016 in connection with U.S. Appl. No. 12/787,283 (U.S. Pat. No. 8,431,549), 7 pages.
Patent Owner Reply to Opposition to Motion to Amend, dated Jul. 19, 2016, in connection with U.S. Appl. No. 12/787,283 (U.S. Pat. No. 8,431,549), 20 pages.
Order Trial Hearing, dated Aug. 22, 2016, in connection with U.S. Appl. No. 12/787,283 (U.S. Pat. No. 8,431,549), 5 pages.
Record of Oral Hearing, dated Nov. 3, 2016, in connection with U.S. Appl. No. 12/787,283 (U.S. Pat. No. 8,431,549), 104 pages.
Inter Partes Review Final Written Decision, filed Dec. 28, 2016, in connection with U.S. Appl. No. 12/787,283 (U.S. Pat. No. 8,431,549), 28 pages.
Restriction Requirement, dated Dec. 30, 2013, in connection with U.S. Appl. No. 13/847,254, 7 pages.
Response, dated Feb. 28, 2014, to Restriction Requirement, dated Dec. 30, 2013, in connection with U.S. Appl. No. 13/847,254, 4 pages.
Office Action, dated Apr. 7, 2014, in connection with U.S. Appl. No. 13/847,254, 17 pages.
Response, dated Jul. 3, 2014, to Office Action, dated Apr. 7, 2014, in connection with U.S. Appl. No. 13/847,254, 18 pages.
Office Action, dated Oct. 14, 2014, in connection with U.S. Appl. No. 13/847,254, 14 pages.
Office Action, dated Feb. 7, 2014, in connection with U.S. Appl. No. 14/100,717, 15 pages.
Response, filed Jun. 9, 2014, to Office Action, dated Feb. 7, 2014, in connection with U.S. Appl. No. 14/100,717, 19 pages.
Notice of Allowance, dated Sep. 22, 2014, in connection with U.S. Appl. No. 14/100,717, 14 pages.
Petition for Inter Partes Review of U.S. Pat. No. 8,895,612, filed Jun. 24, 2015, in connection with U.S. Appl. No. 14/100,717, 68 pages.
Patent Owner Preliminary Response, dated Oct. 12, 2015, to Petition for Inter Partes Review, filed Jun. 24, 2015, in connection with U.S. Appl. No. 14/100,717 (U.S. Patent No. 8,895,612), 70 pages.
Decision Denying Institution of Inter Partes Review, entered Jan. 8, 2016, in connection with U.S. Appl. No. 14/100,717 (U.S. Pat. No. 8,895,612), 23 pages.
Response, dated May 17, 2013, to Office Action issued in connection with Australian Patent Application No. 2007205167, 28 pages.
Notice of Acceptance, dated Jun. 4, 2013, in connection with Australian Patent Application No. 2007205167, 1 page.
Examination Report, dated Apr. 13, 2015, in connection with Australian Patent Application No. 2013206429, 4 pages.
Response, dated Mar. 22, 2016, to Examination Report, dated Apr. 13, 2015, in connection with Australian Patent Application No. 2013206429, 36 pages.
Notice of Acceptance, dated Apr. 14, 2016, in connection with Australian Patent Application No. 2013206429, 3 pages.
Examination Report, dated Jan. 11, 2017, in connection with Australian Patent Application No. 2016205002, 5 pages.
Response, dated Jul. 4, 2013, to Examiner's Report, dated Jan. 4, 2013, in connection with Canadian Patent Application No. 2,635,894, 26 pages.
Examiner's Report, dated Oct. 17, 2013, in connection with Canadian Patent Application No. 2,635,894, 4 pages.
Response, dated Apr. 16, 2014, to Examiner's Report, dated Oct. 17, 2013, in connection with Canadian Patent Application No. 2,635,894, 33 pages.
Examiner's Report, dated Oct. 10, 2014, in connection with Canadian Patent Application No. 2,635,894, 7 pages.
Response, dated Apr. 8, 2015, to Examiner's Report, dated Oct. 10, 2014, in connection with Canadian Patent Application No. 2,635,894, 30 pages.
Examiner's Report, dated Sep. 29, 2015, in connection with Canadian Patent Application No. 2,635,894, 8 pages.
Response, dated Mar. 23, 2016, to Examiner's Report, dated Sep. 29, 2015, in connection with Canadian Patent Application No. 2,635,894, 19 pages.
Examiner's Report, dated May 16, 2016, in connection with Canadian Patent Application No. 2,635,894, 8 pages.
Response, dated Nov. 15, 2016, to Examiner's Report, dated May 16, 2016, in connection with Canadian Patent Application No. 2,635,894, 24 pages.
Examination Report, dated May 10, 2011, in connection with European Patent Application No. 07716309.5, 6 pages.
Response, dated Dec. 14, 2012, to Examination Report, dated Jun. 4, 2012, in connection with European Patent Application No. 07716309.5, 17 pages.
Response, dated Jan. 15, 2014, to Examination Report, dated Jul. 5, 2013, in connection with European Patent Application No. 07716309.5, 19 pages.
Third Party Observations, dated Oct. 31, 2014, and Communication pursuant to Rule 114(2) EPC, dated Nov. 10, 2014, in connection with European Patent Application No. 07716309.5 [Third party observations, Communication and cited references], 22 pages.
Summons to Attend Oral Proceedings, dated Feb. 9, 2015, issued in connection with European Patent Application No. 07716309.5, 4 pages.
Response, dated Oct. 30, 2015, to Summons to Attend Oral Proceedings, dated Feb. 9, 2015, in connection with European Patent Application No. 07716309.5, 98 pages.
Third Party Observations, dated Nov. 11, 2015, and Communication maintaining the date/time for oral proceedings, dated Nov. 12, 2015, in connection with European Patent Application No. 07716309.5, 4 pages.
Response, dated Nov. 27, 2015, to Notice Concerning the Oral Proceedings, dated Nov. 19, 2015, in connection with European Patent Application No. 07716309.5, 67 pages.
Decision to Grant, dated Jun. 23, 2016, issued in connection with European Patent Application No. 07716309.5, 2 pages.
Examination Report, dated Apr. 7, 2014, in connection with European Patent Application No. 13166988.9, 4 pages.
Response, dated Oct. 17, 2014, to Examination Report, dated Apr. 7, 2014, in connection with European Patent Application No. 13166988.9, 13 pages.
Third Party Observations, submitted Nov. 3, 2014, in connection with European Patent Application No. 13166988.9, 2 pages.
Summons to Attend Oral Proceedings, dated Feb. 10, 2015, in connection with European Patent Application No. 13166988.9, 6 pages.
Response, dated Oct. 30, 2015, to Summons to Attend Oral Proceedings, dated Feb. 10, 2015, in connection with European Patent Application No. 13166988.9, 91 pages.
Third Party Observations, dated Nov. 11, 2015, and Communication maintaining the date/time for oral proceedings, dated Nov. 12, 2015, in connection with European Patent Application No. 13166988.9, 4 pages.
Response, dated Nov. 23, 2015, to Summons to Attend Oral Proceedings, dated Feb. 10, 2015, in connection with European Patent Application No. 13166988.9, 13 pages.
Communication from the Patent Office, dated Nov. 30, 2015, in connection with European Patent Application No. 13166988.9, 1 page.
Response, dated Nov. 27, 2015, in connection with European Patent Application No. 13166988.9, 65 pages.
Intention to Grant, dated Dec. 22, 2015, in connection with European Patent Application No. 13166988.9, 7 pages.
Extended European Search Report, dated Aug. 3, 2016, in connection with European Patent Application No. 16172826.6, 13 pages.
Office Action, dated Aug. 30, 2016, in connecton with Korean Patent Application No. 10-2014-7024469 [English translation], 7 pages.
Invalidation Request, filed Jun. 20, 2016, in connection with Chinese Patent Application No. 200780002006 [English translation, document as filed in Chinese and Notice of acceptance of invalidation request as issued in Chinese], 174 pages.
Response, filed Aug. 23, 2016, to Invalidation Request, filed Jun. 20, 2016, in connection with Chinese Patent Application No. 200780002006 [English instructions, document as filed in Chinese and claims as filed in English], 118 pages.

(56) References Cited

OTHER PUBLICATIONS

Notice of Oral Hearing, dated Aug. 31, 2016, in connection with Chinese Patent Application No. 200780002006 [English translation], 5 pages.
Post Hearing Observations, filed Dec. 8, 2016, on Response, filed Aug. 23, 2016, to Invalidation Request, filed Jun. 20, 2016,in connection with Chinese Patent Application No. 200780002006 [English instructions for response, document as filed in Chinese and English translation of filed claims], 57 pages.
Letter/Written Disclosure of the Supplemental Information Disclosure Statement for the above-referenced application, filed herewith on Mar. 7, 2017, 2 pages.
Agarwal et al., "Oxidative stress and renal injury with intravenous iron in patients with chronic kidney disease," Kidney International 65:2279-2289 (2004).
Ahsan et al., "Efficacy of Bolus Intravenous Iron Dextran Treatment in Peritoneal Dialysis Patients Receiving Recombinant Human Erythropoietin," Advances in Peritoneal Dialysis (Khanna ed.) 12:161-166 (1996).
"Report of the ACS Carbohydrate Division Nomenclature Committee," presented at the Annual Meeting of the ACS Committee on Nomenclature, Terminology and Symbols, Apr. 7, 2008, New Orleans, 1 page.
Arond and Frank, "Molecular weight, molecular weight distribution and molecular size of a native dextran," J. Phys. Chem. 58(11):953-957 (1954).
Auerbach et al., "Safety and efficacy of total dose infusion of 1,020 mg of ferumoxytol administered over 15 min," Am. J. Hemat. 88(11):944-947 (2013).
Auerbach et al., "Intravenous Iron Optimizes the Response to Recombinant Human Erythropoietin in Cancer Patients with Chemotherapy-Related Anemia: A Multicenter, Open-Label, Randomized Trial," J. Clinical Oncology 22(7):1301-1307 (2004).
Caligur, "Dextran and Related Polysaccharides," BioFiles 3.10, 17, 7 pages (2008).
Certificate of Analysis, "Anaemex 100 mL HDPE vials," Jan. 14, 1998, 1 page.
Certified English Translation of International Patent Publication No. WO/2004/037865, dated May 27, 2015, 20 pages.
C57BL/6 Mice Nomenclature: C57BL/6NCrl, Charles River Laboratories International, Inc. Pamphlet, 4 pages (2011).
Corrected Declaration of Dr. Adriana Manzi, dated Apr. 21, 2016, 47 pages.
"CosmoFer®," Package insert, Revised Mar. 10, 2005, 2 pages.
Curriculum Vitae of Dr. Adriana Manzi, 12 pages.
Declaration of Robert Linhardt, dated Jun. 17, 2015, 112 pages.
Declaration of Richard P. Lawrence, dated Dec. 5, 2012, 4 pages.
Declaration of Robert Linhardt, dated Jun. 22, 2015, 112 pages.
Declaration of Adriana Manzi, dated Mar. 29, 2016, 47 pages.
Declaration, Deponent: Adriana Manzi, Manzi Errata Sheet, dated Jun. 3, 2016, 3 pages.
Corrected Declaration of Adriana Manzi, dated Apr. 21, 2016, 47 pages.
Declaration of Ellen C. Riemschneider, dated Feb. 4, 2016, 1 page.
Dexferrum® (Iron dextran injection, USP) Rx Only, NDA 40-024/ S-022, American Regent, Inc., pp. 3-11.
Dextran 1 for Injection, European Pharmacoepoeia 5.0, pp. 1408-1409.
Egeli et al., "An evaluation of iron-dextran supplementation in piglets administered by injection on the first, third or fourth day after birth," Res. Vet. Sci. 66(3):179-184 (1999).
"Elephants," San Diego Zoo Animals [online], retrieved on Jun. 13, 2016 from: <URL:animals.sandiegozoo.org/animals/elephant>, 3 pages.
"Executive Bios," Luitpold Pharmaceuticals [online], retrieved on Oct. 7, 2015 from: <URL:luitpold.com/ExecutiveBios.aspx>, 4 pages.
"Feraheme: ferumoxytol injection," revised Mar. 2015, AMAG Pharmaceuticals, Inc. Pamphlet, 4 pages.

New Drug Application (NDA) 22-054 for Injectafer (Ferric Carboxymaltose) for the treatment of iron deficiency anemia in patients with heavy uterine bleeding or postpartum patients, FDA Advisory Committee Briefing Document: Drug Safety and Risk Management Committee, Feb. 1, 2008, 63 pages.
FDA Drug Safety Communications: "FDA strengthens warnings and changes prescribing instructions to decrease the risk of serious allergic reactions with anemia drug Feraheme (feumoxytol)," Mar. 30, 2015, 4 pages.
"Ferrosig: Iron polymaltose 50 mg/ml Drug Product Data Sheet, Zuellig Pharma Limited," [online], retrieved on Feb. 16, 2016 from: URL:medsafe.govt.nz/Profs/Datasheet/f/Ferrosiginj>, prepared Jul. 10, 2003, 6 pages.
Folb, P. I., "The safety of iron dextran and a comparison with iron sucrose for intravenous use: a short report to the World Health Organization Advisory Committee on the safety of medicines," dated Oct. 18, 2004, 5 pages.
Funk et al., "Physical and Chemical Characterization of Therapeutic Iron Containing Materials: A Study of Several Supraparamagnetic Drug Formulations with the β—FeOOH or Ferrihydrite Structure," Hyperfine Interactions 136:73-95 (2001).
Geisser et al., "Investigation on the Dosage/Efficacy Relationship of Iron Dextran in Veal Calves," Drug Res. 41(I), Nr. 1: 32-37 (1991).
Google Scholar Citation Listing for "van Zyl Smit," [online], retrieved on Oct. 7, 2015 from: <URL:scholar.google.com/scholar?h1=en&q=Experience+with+the+use+of+an+iron+polymaltose+%28dextrin%29+complex+given+by+single+total+does+in . . . >, 4 pages.
"Guidelines for administration of IV iron polymaltose in chronic kidney disease via continuous intravenous infusion," Royal Perth Hospital, 3 pages.
Hood et al., "The Safety of Intravenous Iron Dextran (Dexferrum®) During Hemodialysis in Patients with End Stage Renal Disease," Nephrol. Nurs. J. 27(1):41-42 (2000).
Imferon® (iron dextran injection, USP), Fisons Pharmaceuticals, Revised May 1989, 2 pages.
Injectafer® (ferric carboxymaltose injection), American Regent, Inc., Pamphlet revised Jul. 2013, 11 pages.
INFed (iron dextran injection, USP), Schein Pharmaceutical, Inc., revised Sep. 1996, 2 pages.
"Iron Sorbitol Injection," British Pharmacopoeia Omitted Monograph, 4 pages.
Kalra et al., "Iron isomaltoside 1000: a new high dose option for parenteral iron therapy," Port. J. Hypert. 26(1):13-24 (2012).
Keating, G. M., "Ferric Carboxymaltose: A Review of its Use in Iron Deficiency," Drugs 75:101-127 (2015).
Lam-Po-Tang et al., "Icodextrin Hypersensitivity in a CAPD Patient," Peritoneal Dialysis International [online], retrieved on Mar. 25, 2016 from: <URL:pdiconnect.com>, 3 pages.
Lindvall and Andersson, "Studies on a new intramuscular haematinic, iron-sorbitol," Brit. J. Pharmacol. 17:358-371 (1961).
Linhardt and Gunay, "Production and Chemical Processing of Low Molecular Weight Heparins," Seminars in Thrombosis and Hemostasis 25(Suppl. 3):5-16 (1999).
Mamula et al., "Total Dose Intravenous Infusion of Iron Dextran for Iron-Deficiency Anemia in Children With Inflammatory Bowel Disease," Journal of Pediatric Gastroenterology & Nutrition 34(3):286-290 (2002).
McNaught, "Nomenclature of Carbohydrates," Pure & Appl. Chem., 68(10):1919-2008 (1996).
Merriam-Webster Medical Dictionary [online], "hematinic," retrieved on May 28, 2015 from: <URL:merriam-webster.com/medical/hematinic>, 1 page.
Mehmood et al., "Response to intravenous iron in patients with iron deficiency anemia (IDA) and restless leg syndrome (Willis-Ekbom disease)," Sleep Med. 15(12): 1473-1476 (2014).
Pharmacosmos, "MonoFer, Summary of Product Characteristics," revised Mar. 10, 2014, 5 pages.
Morris et al., "Conformation and Intermolecular Interactions of Carbohydrate Chains," Journal of Supramolecular Structure 6:259-274 (1977).

(56) References Cited

OTHER PUBLICATIONS

National Kidney Foundation, "NKF-K/DOQI Clinical Practice Guidelines for Hemodialysis Adequacy: Update 2000," Am. J. Kidney Dis. 37:S7-S64 (suppl 1) (2001).
National Kidney Foundation, "KDOQI Clinical Practice Guidelines and Clinical Practice Recommendations for Anemia in Chronic Kidney Disease," Am. J. Kidney Dis. 47(5):S1-S145 (suppl 3) (2006).
Neiser et al., "Assessment of dextran antigenicity of intravenous iron products by an immunodiffusion assay," Port. J. Hypert. 25(3):219-224 (2011).
Neiser et al., "Physico-chemical properties of the new generation IV iron preparations ferumoxytol, iron isomaltoside 1000 and ferric carboxymaltose," Biometals, published online Mar. 24, 2015, doi: 10.1007/s10534-015-9845-9, 21 pages.
Neiser et al., "Reply to the letter to the editor by Johannes Ring and Rudi Valenta on the article "Assessment of dextran antigenicity of intravenous iron products by an immunodiffusion assay,"" Port. J. Hypert. 26(4):311-312 (2012).
"Orange Book: Approved Drug Products with Therapeutic Equivalence Evaluations, Ferumoxytol," [online] retrieved on Mar. 9, 2015 from: <URL:accessdata.fda.gov/scripts/cder/ob/docs/patexclnew.cfm?Appl_No=022180&Product_No=001&table1=OB_Rx>, 4 pages.
"Orange Book: Approved Drug Products with Therapeutic Equivalence Evaluations, Ferric Carboxymaltose," [online] retrieved on Mar. 9, 2015 from: <URL:accessdata.fda/gov/scripts/cder/ob/docs/patexclnew.cfm?Appl_No=203565&Product_No=001&table1=OB_Rx>, 4 pages.
Parham, P., "The Immune System. Chapter 1: Elements of the immune system and their roles in defense," Garland Publishing/Elsevier Science Ltd., pp. 1-30 (2000).
Peacock and Lindenfeld, "Clinical Practice Guidelines for Maintaining Adequate Iron Status With Intravenous Iron Dextran in Hemodialysis Patients," ANNA J. 26(3):337-343 (1999).
Pink Sheet Pharma Intelligence "Fisons' Opticrom, Imferon May Be Off U.S. Market Until Late 1992 as the company upgrades U.K. manufacturing plant to meet FDA quality control concerns," [online] retrieved on Jun. 13, 2016 from <URL:pharmamedtechbi.com/publications/the-pink-sheet/53/051/fisons-opticrom-imferon-may-be-off-us-market-until-late-1992-as-the-company-upgrade . . . >, posted Dec. 23, 1991, 3 pages.
"Polysaccharide Nomenclature," Pure & Appl. Chem., 54(8):1523-1526 (1982).
"Promit® dextran 1: Consumer Medicine Information," [online] retrieved from <URL:mydr.com.au/cmis/promit-injection>, dated Feb. 7, 2003, Published by MIMS Apr. 2005, 2 pages.
Richter, A. W., "Immune Complex Anaphylaxis Induced by Dextran and its Elimination by Hapten Inhibition," in New Trends in Allergy II, J. Ring et al. (eds.), Springer-Verlag Berlin Heidelberg, pp. 272-283 (1986).
Ring and Valenta, "Letter and Reply to: Neiser et al. (2011) Assessment of dextran antigenicity of intravenous iron products by an immunodiffusion assay," Port. J. Nephrol. Hypert. 26(4), 3 pages (2012).
Roe, F. J. C., "On Potential Carcinogenecity of the Iron Macromolecular Complexes," UICC Monograph Series: Potential Carcinogenic Hazards from Drugs 7:105-116 (1967).
Safety Data Sheet, "Dextran TI Technical Quality," retrieved on May 27, 2015 from: <URL:dextran.net/products/technical-quality/c-24/c-74>, 6 pages.
Sax and Lewis , "Hawley's Condensed Chemical Dictionary, Eleventh Edition," Van Nostrand Reinhold Company Inc., New York, pp. 797, 1081, 1082 (1987).
The Merck Index: An Encylopedia of Chemicals, Drugs and Biologicals, 14th Edition, O'Neil et al. editors, Merck Research Laboratories, pp. 501-502 (2006).
Transcript of the video deposition of Adriana Manzi, Ph.D., dated May 12, 2016, Washington, D.C., 117 pages.

Transcript of the deposition of Robert Linhardt, Ph.D., Case: Pharmacosmos A/S-v-Luitpold Pharmaceuticals, Inc. (PTAB), dated Mar. 2, 2016, New York, New York, 189 pages.
USP Pharmacists' Pharmacopeia, 2nd Edition, The United States Pharmacopeial Convention, Inc., 166 pages (2009).
"USP28-NF23, Official Monographs/Dextran," pp. 601-602, The United States Pharmacopeial Convention, Inc. (2004).
Luitpold Press Release, "Venofer® (iron sucrose injection, USP) receives FDA approval for the treatment of iron deficiency anemia in pre-dialysis patients," American Regent, Jun. 17, 2005, 2 pages.
Vollhardt and Schore, "Organic Chemistry Structure and Function. Chapter 24: Carbohydrates Polyfunctional Compounds in Nature," Fifth Edition, W.H. Freeman and Company, New York, pp. 1096-1138 (2007).
Wallerstein, R. O., "Intravenous Iron-Dextran Complex," Blood 32(4):690-695 (1968).
Walters and Van Wyck, "Benchmarking iron dextran sensitivity: reactions requiring resuscitative medication in incident and prevalent patients," Nephrol. Dial. Transplant. 20:1438-1442 (2005).
Wang et al., "Comparative Risk of Anaphylactic Reactions Associated with Intavenous Iron Products," JAMA 314(19):2062-2068 (2015).
Wang et al., Supplementary Online Content for "Comparative Risk of Anaphylactic Reactions Associated with Intavenous Iron Products," JAMA 314(19):2062-2068 (2015), 19 pages.
Webster's Ninth New Collegiate Dictionary, pp. 19, 20, 985, 994 (1986), 6 pages.
Zager et al., "Parenteral iron nephrotoxicity: Potential mechanisms and consequences," Kidney International 66:144-156 (2004).
Zhang et al., "Tandem MS can Distinguish Hyaluronic Acid from N-Acetylheparosan," J. Am. Soc. Mass Spectrom. 19(1):82-90 (2008).
"21 Years later . . . One group, two strategies. Separation scheduled for Q4 2016," Galenica Group Presentation, Apr. 2016, 48 pages.
Response, dated Nov. 9, 2011, to Search Report, dated May 10, 2011, in connection with European Patent Application No. 07716309.5, 12 pages.
Application for Patent Term Extension, filed Sep. 19, 2013, in connection with U.S. Pat. No. 7,612,109, 75 pages.
Amendment and Response, dated Jun. 9, 2014, to Office Action, dated Feb. 7, 2014, in connection with U.S. Appl. No. 14/100,717, 19 pages.
Certificate Extending Patent Term, in connection with U.S. Pat. No. 6,599,498, dated Mar. 26, 2014, 144 pages.
International Search Report and Written Opinion, dated Aug. 25, 2016, in connection with International Patent Application No. PCT/US2016/34608, 7 pages.
Letter/Written Disclosure of the Supplemental Information Disclosure Statement for the above-referenced application, filed herewith on Jul. 7, 2017, 2 pages.
Aronoff, G.R., "Safety of intravenous iron in clinical practice: implications for anemia management protocols," Journal of the American Society of Nephrology 15:S99-S106 (2004).
Assignment documents of U.S. Appl. No. 11/620,986, dated Mar. 1 and 2, 2007, 4 pages.
Crichton et al., "Iron Therapy with Special Emphasis on Intravenous Administration," UNI-MED, 2nd Ed., cover page, foreword, acknowledgements, preface and contents; and chapters 7, 9, 10 and 11, 40 pages (2005).
Excerpt from Der Bund, edition of Apr. 13, 2005, 3 pages [In German].
Galenica Ltd., "Venofer® approved by FDA ahead of company expectations for use in USA for treatment of iron deficiency anemia in pre-dialysis patients," published Jun. 20, 2005 [online], retrieved on Jun. 19, 2017, from <URL:http://www.evaluategroup.com/Universal/View.aspx?type=Story&id=140890>, 1 page.
Gupte et al., "Iron Deficiency Anemia: Management and Prevention in Children," JK Science 3(4):160-165 (2001).
Hunnius Pharmazeutisches Worterbuch, 8th Edition, catchword "injections," p. 710 (1998), 2 pages [In German].
Manley and McClaran, "Determination of VIT 45 (IND#63,243—American Regent) removal by closed loop in vitro hemodialysis system," Int. J. Artif. Organs 29(11):1062-1066 (2006).

(56) References Cited

OTHER PUBLICATIONS

McCurdy et al., "Parenteral Iron Therapy With Special Reference to a New Preparation for Intramuscular Injection," The New England Journal of Medicine 257(24):1147-1153 (1957).
Nissim, J.A., "Deposition of Iron in the Testes After Administration of an Iron-dextran Complex," The Lancet 268:701-702 (1955).
Paschen, H. W., "Effective anemia treatment involving the administrationg of high intravenous doses of iron," Geburtshilfe Frauenheilkunde 9:604-616 [Original document in German and English language translation], 28 pages.
Preusser et al., "Effects of intravenous ABT-870 (iron (III)-hydroxide oligosaccharide) on mean arterial pressure and heart rate in the anaesthetized beagle: comparison with other iron-containing heamatinic agents," Clin. Exp. Pharmacol. Physiol. 32(12):1020-1026 (2005).
Research Subject Information and Consent Form, entitled "Evaluation of the safety, tolerability and pharmacokinetic profiles of single rising doses and increasing administration rates of ABT-870 in ESRD subjects on chronic hemodialysis with iron deficiency anemia," Sponsored by Abbott Laboratories, dated Apr. 30, 2004, 10 pages.
Screenshot showing document properties of the reproduction of the speech given by Dr. Barbara von Eisenhart-Rothe entitled "Clinical Development Programme of VIT-45," given at a Press conference on Apr. 12, 2005, 2 pages.
Screenshot showing results of Google search for "eisenhart rothe vit-45," 1 page.
Seid et al., "Safety Profile of Iron Carboxymaltose, a New High Dose Intravenous Iron in Patients with Iron Deficiency Anemia," Blood 108(11):3739, 4 pages (2006).
Singh et al., "A comparison between intravenous iron polymaltose complex (Ferrus Hausmann®) and oral ferrous fumarate in the treatment of iron deficiency anaemia in pregnancy," Eur. J. Haematol. 60:119-124 (1998).
Speech given by Dr. Barbara von Eisenhart-Rothe at Galenica Press Conference 5005 on Apr. 12, 2005, Subject: "Clinical Development Programme of VIT-45," 3 pages.
UBS Report on Galenica's Financial Results, dated Apr. 15, 2004, 15 pages.
Van Wyck et al., "A randomized, controlled trial comparing IV iron sucrose to oral iron in anemic patients with nondialysis-dependent CKD," Kidney International 68:2846-2856 (2005).
Notice of Allowance, dated Mar. 8, 2017, in connection with Canadian Patent Application No. 2,635,894, 1 page.
Notice of Opposition to a European Patent, submitted by Hoffman Eitle Patent- und Rechtsanwalte PartmbB on Apr. 10, 2017, in connection with European Patent No. 1 973 549, 20 pages.
Notice of Opposition to a European Patent, submitted by Pharmacosmos Holding A/S on Apr. 13, 2017, in connection with European U.S. Pat. No. 1 973 549, 30 pages.
Notice of Opposition, submitted by Teva Pharmaceutical Industries Ltd. on Apr. 18, 2017, in connection with European Patent No. 1 973 549, 15 pages.
Notice of Opposition, submitted by HGF Limited on Apr. 19, 2017, in connection with European Patent No. 1 973 549, 20 pages.
Notice of Opposition, submitted by STADA Arzneimittel AG on Apr. 20, 2017, in connection with European Patent No. 1 973 549, 42 pages [In German].
Notice of Opposition, submitted by Taylor Wessing LLP on Apr. 20, 2017, in connection with European Patent No. 1 973 549, 29 pages.
Notice of Opposition, submitted by Generics (U.K.) Limited on Apr. 20, 2017, in connection with European Patent No. 1 973 549, 25 pages.
Patent Term Extension Application, filed Sep. 19, 2013, in connection with U.S. Pat. No. 7,612,109, 16 pages.
Notice of Preliminary Rejection, dated Jun. 21, 2017, in connection with Korean Patent Application No. 10-2017-7005732 [English translation and original document in Korean], 22 pages.
Andersson, Clinical Investigations on a new Intramuscular Haematinic, British Medical Journal, 1961, pp. 275-279.
Australian Office Action dated Sep. 15, 2011 in related Application No. AU 2007205167 filed Jan. 8, 2007, 3 pages.
Australian Office Action dated Apr. 13, 2015 in related Application No. AU 2013206429, 4 pages.
Bailie et al., Hypersensitivity reactions and deaths associated with intravenous iron preparations, Nephrol Dial Transplant, 2005, pp. 1443-1449, vol. 20.
Beshara et al., Pharmacokinetics and red cell utilization of $^{52}$Fe/$^{59}$Fe-labelled iron polymaltose in anaemic patients using positron emission tomography, British J. of Haematology, 2003, pp. 853-859, vol. 120.
Canadian Office Action dated Jan. 4, 2013 in related Canadian Application No. 2,635,894 filed Jan. 8, 2007, 4 pages.
Canadian Office Action dated Oct. 17, 2013 in related Canadian Application No. 2,635,894 filed Jan. 8, 2007, 4 pages.
Chinese Office Action dated Apr. 30, 2010 in related Application No. CN200780002006 filed Jan. 8, 2007, English translation, 7 pages.
Cisar et al., Binding properties of immunoglobulin combining sites specific for terminal or nonterminal antigenic determinants in dextran, J Exp Med, 1975, pp. 435-459, vol. 142.
Eschbach et al., NKF-K/DOQI clinical practice guidelines for anemia of chronic kidney disease: update 2000, Am J Kidney Dis, 2001, pp. S182-S238, vol. 37, Supp. 1.
European Official Communication dated Jun. 4, 2012 in related Application No. EP 07716309.5 filed Jan. 8, 2007, 5 pages.
European Office Action dated Jul. 5, 2013 in related Application No. EP07716309.5 filed on Jan. 8, 2007, 5 pages.
European Search Report dated Oct. 21, 2009, in the related application EP 07716309.5.
European Search Report dated Oct. 5, 2011 in related Application No. EP077163093.5 filed Jan. 8, 2007, 6 pages.
European Search Report dated Aug. 7, 2013 in related Application No. EP13166988.9 filed May 8, 2013, 9 pages.
Fielding, Intravenous iron-dextrin in iron-deficiency anaemia, British Medical Journal, 1961, pp. 279-283.
Fishbane, Safety in iron management, Am J Kidney Dis, 2003, 41(6 Suppl 5):S18-S26.
Geisser et al., Structure/Histotoxicity Relationship of Parenteral Iron Preparations, Drug Research, 1992, pp. 1439-1452, vol. 42, No. 2.
Haines et al., Delayed adverse reactions to total-dose intravenous iron polymaltose, Internal Medicine Journal, 2009, pp. 252-255, vol. 39.
Hamstra et al., Intravenous Iron Dextran in Clinical Medicine, JAMA, 1980, pp. 1726-1731, vol. 243, No. 17.
International Search Report and Written Opinion dated Sep. 12, 2007 in related PCT Application No. PCT/US07/00176 filed Jan. 8, 2007, 6 pages.
Kabat et al., Dextran—An Antigen in Man, Journal of Immunology, 1953, pp. 514-532, vol. 70.
Korean Office Action (in Korean and English) dated May 28, 2013 in related Application No. 10-2008-701-6352 filed Jul. 4, 2008, 13 pages.
Kudasheva et al., Structure of carbohydrate-bound polynuclear iron oxyhydroxide nanoparticles in parenteral formulations, Journal of Inorganic Biochemistry, 2004, pp. 1757-1769, vol. 98.
Landry et al., Pharmacokinetic study of Ferumoxytol: A New Iron Replacement Therapy in Normal Subjects and Hemodialysis Patients, Am J Nephrol, 2005, pp. 400-410, vol. 25.
MacDougall, Intravenous administration of iron in epoetin-treated haemodialysis patients—which drugs, which regimen?, Nephrol Dial Transplant, 2000, pp. 1743-1745, vol. 15.
Marchasin et al., The Treatment of Iron-Deficiency Anemia with Intravenous Iron Dextran, Blood, 1964, pp. 354-358, vol. 23 No. 3.
Newnham et al., Safety of iron polymaltose given as a total dose iron infusion, Internal Medicine Journal, 2006, pp. 672-674, vol. 36, No. 10.
Nissenson et al., Controversies in iron management, Kidney International, 2003, pp. S64-S71, vol. 64, Supp. 87.
Sipe et al., Brain iron metabolism and neurodegenerative disorders, Dev. Neuroscience, 2002, pp. 188-196, vol. 24, Nos. 2-3.

(56) References Cited

OTHER PUBLICATIONS

Sofic et al., Increased iron (III) and total iron content in post mortem substantia nigra of parkinsonian brain, J. Neural Transm, 1988, pp. 199-205, vol. 74.
Spinowitz et al., The safety and efficacy of ferumoxytol therapy in anemic chronic kidney disease patients, Kidney International, 2005, pp. 1801-1807, vol. 68.
Van Wyck et al., Making sense: a scientific approach to intravenous iron therapy, J Am Soc Nephrol, 2004, pp. S91-S92, vol. 15, Supp. 2.
Van Wyck, Labile iron: manifestations and clinical implications, J Am Soc Nephrol, 2004, pp. S107-S111, vol. 15., Supp. 2.
Letter/Written Disclosure of the Supplemental Information Disclosure Statement for the above-referenced application, filed herewith on Mar. 14, 2018, 4 pages.
Ali, O., "Commissioning cost-effective delivery of intravenous iron," Prescriber, Navigator Series, pp. 43-46 (2011).
Auerbach, M. and Ballard, H., "Clinical Use of Intravenous Iron: Administration, Efficacy, and Safety," American Society of Hematology, pp. 338-347 (2010).
Bailie, G. R., "Efficacy and safety of ferric carboxymaltose in correcting iron-deficiency anemia: a review of randomized controlled trials across different indications," Arzneimittelforschung 60(6a):386-398 (2010).
Bailie, G. R., "Breaking New Ground in Intravenous Iron Therapy," European Haematology pp. 58-60 (2008).
Chandler et al., "Intravenous Iron Sucrose: Establishing a Safe Dose," American Journal of Kidney Diseases 38(5):988-991 (2001).
Crichton et al., "Iron Therapy with Special Emphasis on Intravenous Administration: Iron Therapy and Oxidative Stress," UNI-MED, 2nd Ed., 4 pages (2005).
"Comparative Test vs. DI (U.S. Pat. No. 3,639,588)," 2 pages.
Drugs.com, "Gleptosil Injection (Canada)," [cited Nov. 15, 2017]; available from: <URL:drugs.com/vet/gleptosil-injection-can.html, 3 pages.
European Medicines Agency Science Medicines Health, "CHMP Assessment Report: Rienso, Common name: Ferumoxytol," dated Apr. 19, 2012, 79 pages.
Falbe et al., "Rompp Lexikon Chemie," p. 213, Georg Thieme Verlag [original document in German with certified English translation], 5 pages (1997).
Notice of Recordation of Assignment, dated Mar. 29, 2006, in connection with U.S. Appl. No. 60/757,119, 7 pages.
Accessdata, "Orange Book: Approved Drug Products with Therapeutic Equivalence Evaluations," [cited Nov. 21, 2017]; [online] available from: <URL:accessdata.fda.gov/scripts/cder/ob/patent_info.cfm?Product_No=001&Appl_No=0221 . . . , 3 pages.
Pugh-Clarke et al., "An Evidence-Based Approach to Anaemia Management in Predialysis Chronic Kidney Disease," Journal of Renal Care 35(s2):29-31 (2009).
Tagboto et al., "The efficacy of a single dose of intravenous ferric carboxymaltose (Ferinject®) on Anaemia in a pre-dialysis population of chronic kidney disease patients," Journal of Renal Care 35(1):18-22 (2009).
Reply of the Patent Proprietor Vifor (International) AG, filed Feb. 2, 2018, to the Notices of Opposition, dated May 26, 2017, in connection with European Patent No. 1 973 549, 169 pages.
Letter/Written Disclosure of the Supplemental Information Disclosure Statement for the above-referenced application, filed herewith on Jan. 26, 2018, 2 pages.
Excerpt of prosecution history of European Patent Application No. EP07716309.5, 4 pages.
Excerpt of prosecution history of European Patent Application No. EP07716309.5, 7 pages.
Excerpt of prosecution history of U.S. Pat. No. 7,754,702, 99 pages.
Prosecution history of U.S. Pat. No. 8,431,549, 244 pages.
Excerpt of prosecution history of U.S. Pat. No. 8,431,549, 75 pages.
Prosecution history of U.S. Pat. No. 8,895,612, 237 pages.
Excerpt of prosecution history of U.S. Pat. No. 8,895,612, 48 pages.

Excerpt from Der Bund, edition of Apr. 13, 2005, 3 pages [English translation].
Hunnius Pharmazeutisches Worterbuch, 8th Edition, catchword "injections," p. 710 (1998) [English translation, 1 page].
IUPAC Polysaccharide Nomenclature Recommendations 1980, 4 pages.
Monofer Summary of Product Characteristics, revised Mar. 10, 2014, 5 pages.
Prosecution history of U.S. Appl. No. 14/683,415, 192 pages.
Prosecution history of U.S. Appl. No. 13/847,254, 251 pages.
Prosecution history of U.S. Pat. No. 7,754,702, 343 pages.
USPTO Patent Full-Text and Image Database, "Help on the Quick Search Page," 5 pages.
Van Wyck et al., "Labile iron in parenteral iron formulations: a quantitative and comparative study," Nephrol. Dial. Transplant. 19:561-565 (2004).
American Regent Press Release, "American Regent Announces Enrollment of First Patient in Phase 3 Trial to Investigate Injectafer® (Ferric Carboxymaltose) as Treatment for Heart Failure with Iron Deficiency," Published Apr. 24, 2017 [online]; Retrieved on Oct. 17, 2017, from URL:americanregent.com/Documents/ARNews/American_Regent_HEART-FID_Clinical_Trial_FPI_Press_Release_FINAL-4_21.pdf , 3 pages.
Luitpold Press Release, "American Regent Announces an FDA-Approved Pediatric Indication Exclusivity for Venofer (Iron Sucrose Injection, USP)," Published Oct. 19, 2012 [online]; Retrieved on Oct. 16, 2017, from <URL:luitpold.com/documents/news/SlaqafRbOnQomqzQJHcw==.pdf, 16 pages.
Luitpold Press Release, "American Regent announces a new FDA-Approved Pediatric Indication for Venofer® (Iron Sucrose Injection, USP)," Published Sep. 26, 2012 [online]; Retrieved on Oct. 16, 2017, from URL:luitpold.com/documents/news/INMbGpxMEVk=.pdf, 16 pages.
Luitpold Press Release, "American Regent announces FDA approval for Venofer® in the treatment of Iron Deficiency Anemia in Peritoneal Dialysis Patients," Published Oct. 17, 2005 [online]; Retrieved on Oct. 16, 2017, from URL:luitpold.com/documents/news/TdpFxv064UU=.pdf, 2 pages.
Luitpold Press Release, "American Regent announces new PDUFA action date for Injectafer® (ferric carboxymaltose injection) NDA for the treatment of iron deficiency anemia," Published Apr. 8, 2013 [online]; Retrieved on Oct. 16, 2017, from URL:luitpold.com/documents/news/GvrNvPISehlqdL9Ldjhgkw==.pdf, 2 pages.
Luitpold Press Release, "American Regent's Injectafer® (Ferric Carboxymaltose Injection) Assigned Q Code by Centers for Medicare and Medicaid Services," Published May 1, 2014 [online]; Retrieved on Oct. 16, 2017, from URL:luitpold.com/documents/news/1E7UsdIztevebKp+Zgn07w==.pdf, 5 pages.
Luitpold Press Release, "American Regent Resumes Shipment of Injectable Products," Published May 6, 2011 [online]; Retrieved on Oct. 16, 2017, from URL:luitpold.com/documents/news/NSQdwNibxrY=.pdf, 2 pages.
Luitpold Press Release, "American Regent Resumes Shipment of Venofer® (iron sucrose injection, USP)," Published May 3, 2011 [online]; Retrieved on Oct. 16, 2017, from URL:luitpold.com/documents/news/1KZCDYvETdw=.pdf, 1 page.
Luitpold Press Release, "FDA Advisory Committee Supports Favorable Risk-Benefit Profile for Injectafer™ (Ferric Carboxymaltose Injection) Under Certain Indications for Use," Published Feb. 4, 2008 [online]; Retrieved on Oct. 16, 2017, from URL:luitpold.com/documents/news/z+dV+KHfJMc=.pdf, 2 pages.
Luitpold Press Release, "FDA Assigns PDUFA Date for Injectafer® (ferric carboxymaltose injection) NDA," Published Dec. 15, 2011 [online]; Retrieved on Oct. 16, 2017, from URL:luitpold.com/documents/news/MIPDRvQ+mjk=.pdf, 2 pages.
Luitpold Press Release, "Important Drug Product Notice: Luitpold Pharmaceuticals, Inc. Announces Temporary Suspension of Distribution and Manufacture of Drug Products," Published Apr. 21, 2011 [online]; Retrieved on Oct. 16, 2017, from URL:luitpold.com/documents/news/0eLJ1VKb5rc=.pdf, 1 page.
Luitpold Press Release, "Injectafer® (ferric carboxymaltose injection) receives US FDA approval for the treatment of Iron Deficiency Anemia," Published Jul. 25, 2013 [online]; Retrieved on Oct. 16,

(56) References Cited

OTHER PUBLICATIONS 2017, from URL:luitpold.com/documents/news/ 9Fo4fHAOE0SHYfSyNdTbkw==.pdf, 3 pages.
Luitpold Press Release, "Luitpold Pharmaceuticals/American Regent and Fresenius Medical Care sign agreements for exclusive sublicense of Venofer® in U.S.," Published Jul. 9, 2008 [online]; Retrieved on Oct. 16, 2017, from URL:luitpold.com/documents/news/VysTqXcRR2s=.pdf, 2 pages.
Luitpold Press Release, "Luitpold Pharmaceuticals/American Regent announces Closing of exclusive sublicense of Venofer® by Fresenius Medical Care in U.S.," Published Sep. 16, 2008 [online]; Retrieved on Oct. 16, 2017, from URL:luitpold.com/documents/news/YHGinfwHw1E=.pdf, 2 pages.
Luitpold Press Release, "Luitpold Pharmaceutical's INJECTAFER™ (ferric carboxymaltose injection) receives non-approvable letter from FDA," Published Mar. 12, 2008 [online]; Retrieved on Oct. 16, 2017, from URL:luitpold.com/documents/news/wSxU1jvMZ08=.pdf, 2 pages.
Luitpold Press Release, "Luitpold Pharmaceuticals, Inc. Receives Complete Response Letter for Injectafer® from the U.S. Food and Drug Administration," Published Jul. 26, 2012 [online]; Retrieved on Oct. 16, 2017, from URL:luitpold.com/documents/news/RGFqg0SyN9s=.pdf, 2 pages.
Luitpold Press Release, "Luitpold Pharmaceuticals, Inc. Submits Injectafer® NDA to the U.S. Food and Drug Administration," Published Oct. 13, 2011 [online]; Retrieved on Oct. 16, 2017, from URL:luitpold.com/documents/news/MC0f+G2pkOM=.pdf, 2 pages.
Application for Patent Term Extension, filed Jul. 24, 2009, in connection with U.S. Pat. No. 6,599,498, 121 pages.
Amendment and Response, dated Jun. 9, 2014, and Office Action, dated Feb. 7, 2014, in connection with U.S. Appl. No. 14/100,717, 34 pages.
Notice of Federal Circuit Appeal, filed Mar. 2, 2017 by Luitpold Pharmaceuticals, Inc., in connection with U.S. Pat. No. 7,754,702, 5 pages.
Notice of Federal Circuit Appeal, filed Mar. 1, 2017 by Luitpold Pharmaceuticals, Inc., in connection with U.S. Pat. No. 8,431,549, 4 pages.
Brief of Appellant Luitpold Pharmaceuticals, Inc., filed Jul. 27, 2017, in connection with U.S. Pat. Nos. 7,754,702 and 8,431,549, 164 pages.
Principal and Response Brief of Appellee and Cross-Appellant Pharmacosmos A/S, filed Sep. 5, 2017, in connection with U.S. Pat. Nos. 7,754,702 and 8,431,549, 86 pages.
Corrected Response and Reply Brief of Appellant Luitpold Pharmaceuticals, Inc., filed Oct. 30, 2017, in connection with U.S. Pat. Nos. 7,754,702 and 8,431,549, 62 pages.
Citation of Supplemental Authority, filed Nov. 2, 2017 by Pharmacosmos A/S in connection with U.S. Pat. Nos. 7,754,702 and 8,431,549, 2 pages.
Response, filed Nov. 6, 2017 by Luitpold Pharmaceuticals, Inc., to the Citation of Supplemental Authority, filed Nov. 2, 2017 by Pharmacosmos A/S in connection with U.S. Pat. Nos. 7,754,702 and 8,431,549, 2 pages.
Reply Brief of Cross-Appellant Pharmacosmos A/S, filed Nov. 13, 2017, in connection with U.S. Pat. Nos. 7,754,702 and 8,431,549, 23 pages.
Joint Appendix, filed Nov. 17, 2017, in connection with U.S. Pat. Nos. 7,754,702 and 8,431,549, pp. 1-400.
Response, filed Jan. 10, 2018, to Examination Report, dated Jan. 11, 2017, in connection with Australian Patent Application No. 2016205002, 23 pages.
Examiner's Report, dated Jun. 28, 2017, in connection with Canadian Patent Application No. 2,953,964, 9 pages.
Response, filed Dec. 28, 2017, to Examiner's Report, dated Jun. 28, 2017, in connection with Canadian Patent Application No. 2,953,964, 36 pages.
Response, filed Dec. 21, 2017, to Notice of Preliminary Rejection, dated Jun. 21, 2017, in connection with Korean Patent Application No. 10-2017-7005732 [English instructions, original document as filed in Korean and English translation of amended claims], 55 pages.
Notice of Acceptance, dated Jan. 11, 2018, in connection with Australian Patent Application No. 2016205002, 2 pages.
Joint Appendix, filed Nov. 17, 2017, in connection with U.S. Pat. Nos. 7,754,702 and 8,431,549, pp. 401-723.
Letter/Written Disclosure of the Supplemental Information Disclosure Statement for the above-referenced application, filed herewith on Mar. 27, 2018, 2 pages.
Notice of Opposition, submitted by STADA Arzneimittel AG dated Apr. 20, 2017, in connection with European Patent No. 1 973 549 [English translation], 26 pages.
Response of Opponent Pharmacosmos Holding A/S, filed Mar. 9, 2018, to Reply of Patent Proprietor Vifor (International) AG, filed Feb. 2, 2018, in connection with European Patent No. 1 973 549, 15 pages.
Letter/Written Disclosure of the Supplemental Information Disclosure Statement for the above-referenced application, filed herewith on May 2, 2018, 2 pages.
Order for Case Dismissal of PTAB Appeal No. IPR2015-01490, filed Apr. 12, 2018, in connection with U.S. Pat. No. 7,754,702, 2 pages.
Notice of Entry of Judgement Without Opinion, and Judgement, dated Apr. 12, 2018, in connection with PTAB Appeal Nos. IPR2015-01490 (U.S. Pat. No. 7,754,702) and IPR2015-01493 (U.S. Pat. No. 8,431,549), 5 pages.
Letter/Written Disclosure of the Supplemental Information Disclosure Statement for the above-referenced application, filed herewith on May 8, 2018, 3 pages.
Notice of Opposition by Pharmacosmos Holding A/S, dated Apr. 30, 2018, in connection with Australian Patent Application No. 2016205002, 3 pages.
Notice of Final Rejection, dated Apr. 30, 2018, in connection with Korean Patent Application No. 10-2017-7005732 [English translation and original document in Korean; Ref. 1=US 2004/0180849; Ref. 2=Spinowitz et al., Kidney International 68:1801-1807 (2005); Ref. 3=KR 10-2005-0070014], 9 pages.
Letter/Written Disclosure of the Supplemental Information Disclosure Statement for the above-referenced application, filed herewith on Apr. 23, 2018, 2 pages.
Examiner's Report, dated Mar. 9, 2018, in connection with corresponding Canadian Patent Application No. 2,953,964, 5 pages.
Letter/Written Disclosure of the Supplemental Information Disclosure Statement for the above-referenced application, filed herewith on Jun. 13, 2018, 2 pages.
Summons to Attend Oral Proceedings Pursuant to Rule 115(1) EPC, dated Jun. 5, 2018, in connection with corresponding European Patent No. 1973549, 8 pages.
Letter/Written Disclosure of the Supplemental Information Disclosure Statement for the above-referenced application, filed herewith on Jul. 26, 2018, 2 pages.
Third Party Observation for Application No. EP20070716309, submitted Jul. 23, 2018, in connection with corresponding European Patent No. 1973549, 3 pages.
Letter/Written Disclosure of the Supplemental Information Disclosure Statement for the above-referenced application, filed herewith on Sep. 7, 2018, 5 pages.
Statement of Grounds and Particulars, filed Jul. 30, 2018, in support of the Notice of Opposition, filed Apr. 30, 2018 by Pharmacosmos Holding A/S, in connection with Australian Patent Application No. 2016205002, 25 pages.
Alvares et al., "Evaluation of cardiac function in iron deficiency anemia before and after total dose iron therapy," J. Assoc. Physicians India 48(2):204-206 (2000).
Bingham et al., "Increased transfer of iron to the fetus after total dose infusion of iron dextran during pregnancy," J. Clin. Pathol. 36(8):907-909 (1983).
British Pharmacopoeia, Entry for Iron Dextran Injection, vol. II, pp. 2252-2253 (2002).
Certified English language translation of International Patent Publication No. WO 2004/037865, 20 pages.

(56) References Cited

OTHER PUBLICATIONS

Chertow et al., "On the relative safety of parenteral iron formulations," Nephrol. Dial. Transplant 19(6):1571-1575 (2004).
CosmoFer® Summary of Product Characteristics, Dec. 2005, 13 pages.
CosmoFer® Summary of Product Characteristics (SmPC), Sep. 2003, 10 pages.
Grimes, A.J. and Hutt, M.S.R., "Metabolism of $^{59}$Fe-dextran complex in human subjects," Br. Med. J. 2(5053):1074-1077 (1957).
Leuillet, M. and Salmon-Legagneur, E., "Sur L'Utilisation D'Un Composé De Fer Dextrane Hydrogéné Par Injection Chez La Truie En Gestation Et En Lactation," Ann. Zootech. 17(1):59-70 (1968) [In French].
Certified English language translation of Leuillet, M. and Salmon-Legagneur, E. (1968) Ann, Zootech. 17(1):59-70, 12 pages.
London, E., "The molecular formula and proposed structure of the iron-dextran complex, imferon," J. Pharm. Sci. 93(7):1838-1846 (2004).
Sergejew et al., "Chelator-induced iron excretion in iron-overloaded marmosets," Br. J. Haematol. 110(4):985-992 (2000).
Silverberg et al., "Erythropoietin should be part of congestive heart failure management," Kidney Int. 64(Suppl. 87):S40-S47 (2003).
Test for Iron Absorption, British Pharmacopoeia, p. 1364 (1968).
Ullmann's Encyclopedia of Industrial Chemistry, Sixth Edition, vol. 10, pp. 435-440 (2003).
Ullmann's Encyclopedia of Industrial Chemistry, Fifth Edition, vol. A8, pp. 449-454 (1987).
Written Submissions of Taylor Wessing LLP, filed on Sep. 3, 2018, in response to the Reply of the Patent Proprietor Vifor, dated Feb. 2, 2018, to the Notices of Opposition, in connection with European Patent No. 1 973 549, 18 pages.
Seid et al., Blood 108(11):3739 (2006), obtained from the British Library with a public availability date stamp and covering letter showing availability to the public on Dec. 6, 2006, 6 pages.
Van Wyck et al., "Intravenous Ferric Carboxymaltose Compared with Oral Iron in the Treatment of Postpartum Anemia," Obstetrics & Gynecology 110(2), Part 1, pp. 267-278 (2007).
Screenshot of Luitpold Pharmaceuticals homepage (<URL:luitpold.com/), showing the relationship between Luitpold and American Regent Inc., 1 page.
Extract from ClinicalTrials.gov website showing the details of trial No. NCT00396292, entitled "Comparison of the Safety and Efficacy of Intravenous Iron Versus Oral Iron in Subjects Who Display Postpartum Anemia," last updated Feb. 5, 2018, 16 pages.
Extract from ClinicalTrials.gov website showing the details of trial No. NCT02397057 for the treatment of Restless Legs Syndrome, entitled "Placebo-Controlled Study to Investigate the Efficacy & Safety of Injectafer in the Treatment of RLS," last updated Jan. 24, 2018, 8 pages.
Extract of MHRA Public Assessment Report for Ferinject® 50mg iron/ml solution for injection/infusion (Ferric carboxymaltose), 6 pages.
Funk et al., "The new generation of intravenous iron: chemistry, pharmacology, and toxicology of ferric carboxymaltose," Arzneimittelforschung 60(6a):345-353 (2010).
Declaration by Dr. Kim Nordfjeld of Pharmacosmos A/S (Denmark), dated Sep. 11, 2018, submitted in conncection with the Opposition to Australian Patent Application No. 2016205002, 3 pages.
Declaration by Hans Andreasen of Pharmacosmos A/S (Denmark), dated Sep. 13, 2018, submitted in connection with the Opposition to Australian Patent Application No. 2016205002, 1 page.
Written Submission of HGF Limited, filed on Sep. 21, 2018, in connection with the Opposition to European Patent No. 1 973 549, 10 pages.
CosmoFer® UK Product Leaflet, 2001, 2 pages.
Silverberg et al., "The role of anemia in the progression of congestive heart failure. Is there a place for erythropoietin and intravenous iron?" J. Nephrol. 17(6):749-761 (2004).
Letter/Written Disclosure of the Supplemental Disclosure Statement for the above-referenced application, filed herewith on Sep. 28, 2018, 4 pages.
Declaration by Kathryn Barbara Morris of Griffith Hack, dated Oct. 25, 2018, submitted in connection with the Opposition to Australian Patent Application No. 2016205002, 16 pages.
Amended Statement of Grounds and Particulars, dated Oct. 3, 2018, in support of the Notice of Oppositionm filed Apr. 30, 2018 by Pharmacosmos Holding A/S, in connection with Australian Patent Application No. 2016205002, 43 pages.
Letters Patent, issued Sep. 28, 2018, in connection with corresponding Korean Patent Application No. 10-2017-7005732 [English translation and original document in Korean], 3 pages.
Notice of Preliminary Rejection, dated Sep. 18, 2018, in connection with corresponding Korean Patent Application No. 10-2018-7018660 [English translation and original document in Korean], 11 pages.
Letter/Written Disclosure of the Supplemental Information Disclosure Statement for the above-referenced application, filed herewith on Nov. 6, 2018, 6 pages.
Written Submission of Hoffman Eitle Patent, filed on Nov. 28, 2018, in response to the Summons to Attend Oral Proceedings Pursuant to Rule 115(1) EPC, dated Jun. 5, 2018, in connection with the Opposition to Eurogean Patent No. 1 973 549, 16 pages.
Written Submission of Opponent Pharmacosmos Holding A/S, filed on Nov. 29, 2018, in response to the Summons to Attend Oral Proceedings Pursuant to Rule 115(1) EPC, dated Jun. 5, 2018, in connection with the Opposition to European Patent No. 1 973 549, 37 pages.
Written Submission of Opponent Generics (U.K.) Limited, filed on Nov. 30, 2018, in response to the Summons to Attend Oral Proceedings Pursuant to Rule 115(1) EPC, dated Jun. 5, 2018, in connection with the Opposition to European Patent No. 1 973 549, 6 pages.
Written Submission of Patent Proprietor Vifor (International) AG, filed Nov. 30, 2018, in response to the Summons to Attend Oral Proceedings Pursuant to Rule 115(1) EPC, dated Jun. 5, 2018, in connection with the Opposition to European Patent No. 1 973 549, 187 pages.
Letter/Written Disclosure of the Supplemental Information Disclosure Statement for the above-referenced application, filed herewith on Dec. 19, 2018, 3 pages.
Paul at al., "Synthesis of Ultrasmall Superparamagnetic Iron Oxides Using Reduced Polysagqharides," Bioconjugate Chem. 15:394-401 (2004).
Office Action, dated Jan. 7, 2019, in connection with U.S. Appl. No. 16/192,681, 19 pages.
Declaration by Kathryn Barbara Morris of Griffith Hack, dated Jan. 22, 2019, submitted in connection with the Opposition to Australian Patent Application No. 2016205002 [Exhibits KBM-5, KBM-6, KBM-7, KBM-8 and KBM-9 appended], 225 pages.
Declaration of Vito Ferro, dated Jan. 29, 2019, submitted in connection with the Opposition to Australian Patent Application No. 2016205002 [Exhibits VF-1, VF-2, VF-3, VF-4, VF-5, VF-6, VF-7, VF-8, VF-9, VF-10, VF-11, VF-12 and VF-13 amended], 266 pages.
Protest under Section 10 of the Patent Rules, filed on Dec. 5, 2018 by ROBIC, L.L.P., against Canadian Patent Application No. 2,953,964, 42 pages.
Written Submission of Opponent Taylor Wessing LLP, submitted Jan. 23, 2019, in connection with the Opposition to European Patent No. 1 973 549, 24 pages.
Written Submission of Patent Proprietor Vifor (International) AG, submitted Jan. 28, 2019, in preparation of the oral proceedings and in response to the submission of Opponent Pharmacosmos Holding A/S, dated Nov. 29, 2018, in connection with the Opposition to European Patent No. 1 973 549, 7 pages.
Information about the result of the Oral Proceedings of Jan. 30, 2019, dated Jan. 31, 2019, in connection with the Opposition to Eurogean Patent No. 1 973 549, 1 page.
Letter/Written Disclosure of the Supplemental Information Disclosure Statement for the above-referenced application, filed herewith on Feb. 19, 2019, 6 pages.

(56) References Cited

OTHER PUBLICATIONS

Declaration of Simon David Roger, dated Feb. 27, 2019, submitted in connection with the Opposition by Pharmacosmos Holding A/S to Australian Patent Application No. 2016205002 [Exhibits SDR-01 to SDR-10 appended], 232 pages.
Examiner's Report, dated Mar. 13, 2019, in connection with corresponding Canadian Patent Application No. 2,953,964, 6 pages.
Interlocutory Decision in Opposition proceedings, dated Feb. 28, 2019, in connection with the Opposition to European Patent No. 1 973 549, 78 pages.
Letter/Written Disclosure of the Supplemental Information Disclosure Statement for the above-referenced application, filed herewith on Apr. 1, 2019, 13 pages.
Notice of Paragraph IV Certification, re: Ferric Carboxymaltose, dated May 7, 2019, in connection with U.S. Pat. Nos. 7,612,109, 7,754,702, 8,895,612 and 9,376,505 [referenced WIPO publications and published papers appended], 421 pages.
Voluntary Amendment, filed Apr. 24, 2019, in connection with corresponding Australian Patent Application No. 2016205002, 11 pages.
Letter, dated May 20, 2019, from IP Australia, indicating that a Stay of the Opposition to Australian Patent Application No. 2016205002, requested in the Voluntary Amendment filed Apr. 24, 2019, will be granted, 2 pages.
Comments, filed May 21, 2019, by Opponent Pharmacosmos Holding A/S, in response to the Voluntary Amendment, filed Apr. 24, 2019, by Applicant American Reagent, Inc., in connection with the Opposition to corresponding Australian Patent Application No. 2016205002, 4 pages.
Response of Opponent Pharmacosmos Holding A/S, filed May 24, 2019, to the intention to grant a stay in the Opposition Proceedings in connection with Australian Patent Application No. 2016205002, dated May 20, 2019, 1 page.
Direction made to stay the Opposition to Australian Patent Application No. 2016205002, dated May 30, 2019, 1 page.
Letter, dated Jun. 3, 2019, from IP Australia, indicating that leave to amend the specification, requested in the Voluntary Amendment filed Apr. 24, 2019, will be granted, in connection with Australian Patent Application No. 2016205002, 1 page.
Notice of Appeal, filed by Opponent Pharmacosmos Holding A/S on Apr. 12, 2019, against the Interlocutory Decision, dated Feb. 28, 2019, in connection with the Opposition to corresponding European Patent No. 1 973 549, 5 pages.
Notice of Appeal, filed by Opponent Teva Pharmaceutical Industries Ltd. on Apr. 23, 2019, against the Interlocutory Decision, dated Feb. 28, 2019, in connection with the Opposition to corresponding European Patent No. 1 973 549, 3 pages.
Notice of Appeal, filed by Opponent Taylor Wessing LLP on Apr. 26, 2019, against the Interlocutory Decision, dated Feb. 28, 2019, in connection with the Opposition to corresponding European Patent No. 1 973 549, 3 pages.
Notice of Appeal, filed by Opponent Stada Arzneimittel AG on May 2, 2019, against the Interlocutory Decision, dated Feb. 28, 2019, in connection with the Opposition to European Patent No. 1 973 549 [machine-generated English language translation and original document in German], 10 pages.
Notice of Appeal, filed by Opponent Generics [UK] Limited on May 3, 2019, against the Interlocutory Decision, dated Feb. 28, 2019, in connection with the Opposition to corresponding European Patent No. 1 973 549, 4 pages.
Notice of Appeal, filed by Opponent Hoffmann Eitle Patent on May 7, 2019, against the Interlocutory Decision, dated Feb. 28, 2019, in connection with the Opposition to corresponding European Patent No. 1 973 549, 5 pages.
Notice of Appeal, filed by Patent Proprietor Vifor (International) AG on May 10, 2019, against the Interlocutory Decision, dated Feb. 28, 2019, in connection with the Opposition to corresponding European Patent No. 1 973 549, 5 pages.
Notice of Final Rejection, issued Apr. 29, 2019, in connection with corresponding Korean Patent Application No. 10-2018-7018660 [English translation and original document in Korean: Ref. 1 = U.S. 2004/0180849; Ref. 2 = Spinowitz et al. (2005) *Kidney International* 68:1801-1807], 8 pages.
Letter/Written Disclosure of the Supplemental Information Disclosure Statement for the above-referenced application, filed herewith on Jun. 6, 2019, 6 pages.
Certified File History of U.S. Appl. No. 12/787,283 (issued as U.S. Pat. No. 8,431,549), certified on Mar. 27, 2019, 362 pages.
Complaint for Patent Infringement, filed Aug. 2, 2019 in the U.S. District Court for the District of New Jersey, by Plaintiffs Vifor (International) AG and American Regent, Inc., against Defendant Sandoz Inc., in connection with U.S. Pat. Nos. 7,612,109, 7,754,702, 8,895,612 and 9,376,505 [Exhibits A-D, and documents 1-5 and 1-6 appended], 78 pages.
Complaint for Patent Infringement, filed Jun. 20, 2019 in the U.S. District Court for the Northern District of West Virginia, by Plaintiffs Vifor (International) AG and American Regent, Inc., against Defendant Mylan Laboratories Ltd., in connection with U.S. Pat. Nos. 7,612,109, 7,754,702, 8,895,612 and 9,376,505 [Exhibits A-D and documents 1-5, 3, 4 and 6 appended], 79 pages.
Complaint for Patent Infringement, filed Jun. 18, 2019 in the U.S. District Court for the District of New Jersey, by Plaintiffs Vifor (International) AG and American Regent, Inc., against Defendant Mylan Laboratories Ltd., in connection with U.S. Pat. Nos. 7,612,109, 7,754,702, 8,895,612 and 9,376,505 [Exhibits A-D, documents 1-5, 1-6 and documents 2 to 6 appended], 82 pages.
Curriculum Vitae of Robert Linhardt, Ph.D., 115 pages.
Expert Declaration of Robert Linhardt, Ph.D., dated Jun. 13, 2019, 20 pages.
Motion to Stay the Second Filed Suit in the Northern District of West Virginia against Defendant Mylan Laboratories Ltd., filed on Jul. 10, 2019 by Plaintiffs Vifor (International) AG and American Regent, Inc., in connection with U.S. Pat. Nos. 7,612,109, 7,754,702, 8,895,612 and 9,376,505 [Exhibits 1-7 appended], 148 pages.
Mylan Laboratories Ltd.'s Answer, Separate Defenses, and Counterclaims to Vifor (International) AG and American Regents, Inc.'s Complaint, filed Jul. 26, 2019 in the U.S. District Court for the District of New Jersey, in connection with U.S. Pat. Nos. 7,612,109, 7,754,702, 8,895,612 and 9,376,505 [Documents 16-1 and 17 appended], 31 pages.
Order Granting Plaintiffs' Unopposed Motion to Stay the Second-Filed Suit in the Northern District of West Virginia and Staying the Case, dated Jul. 26, 2019, in connection with U.S. Pat. Nos. 7,612,109, 7,754,702, 8,895,612 and 9,376,505, 2 pages.
Patent Assignment recorded at Reel: 048067 Frame: 0271—Assignment and Change of Name from Luitpold Pharmaceuticals, Inc. to American Regent, Inc., execution dated Jan. 2, 2019, 6 pages.
Petition for Inter Partes Review of U.S. Pat. No. 8,431,549, submitted by Petitioner Pharmacosmos A/S on Jun. 14, 2019 (Case No. IPR2019-01142), 44 pages.
Final Office Action, dated Jul. 8, 2019, in connection with U.S. Appl. No. 16/192,681, 15 pages.
Notice of Opposition, filed Aug. 13, 2019, by Opponent Pharmacosmos Holding A/S, to the allowance of the amendment to Australian Patent Application No. 2016205002, filed Apr. 24, 2019, 2 pages.
Examination Report, dated Jun. 15, 2019, in connection with Australian Patent Application No. 2018202715, 5 pages.
Statement of Grounds of Appeal, filed by Opponent Teva Pharmaceutical Industries Ltd. on Jul. 2, 2019, further to the Notice of Appeal, filed on Apr. 23, 2019, against the Interlocutory Decision, dated Feb. 28, 2019, in connection with Opposition to European Patent No. 1 973 549 [D72 appended; D13=WO 2007/081744; D33=U.S. Appl. No. 60/757,119; D2a=U.S. Pat. No. 7,612,109; D2b=WO 2004/037865; D2c=CA 2493806; D3=Marchasim et al. (1964) *Blood* 23(3):354-358; D4=U.S. 2003/0232084; D12=Spinowitz et al. (2005) *Kidney International* 68:1801-1907; and D14=Landry et al. (2005) *American Journal of Nephrology* 25(4):400-410], 18 pages.
Statement of Grounds of Appeal, filed by Opponent Taylor Wessing LLP on Jul. 5, 2019, further to the Notice of Appeal, filed on Apr. 26, 2019, against the Interlocutory Decision, dated Feb. 28, 2019, in connection with the Opposition to European Patent No. 1 973 549 [D64=Extract of MHRA Public Assessment Report for Ferinject®

(56) References Cited

OTHER PUBLICATIONS

50mg iron/ml solution for injection/infusion; D9=Speech given by Dr. Barbara von Eisenhart-Rothe at Galenica Press Conference 5005 on Apr. 12, 2005, Subject; "Clinical Development Programme of VIT-45;" D9d=U.S. 2006/0116349; D9e=Manley and McClaran (2006) *Int. J. Artif. Organs* 29(11):1062-1066; D27=Seid et al. (2006) *Blood* 108(11):3739; D59=Copy of Seid et al. (2006) *Blood* 108(11):3739 with a public availability date stamp; D2a=U.S. Pat. No. 7,612,109; D2b=WO 2004/037865; D2c=CA 2493806; D1=U. S. Pat. No. 3,639,588; and D32=U.S. 2004/0180849], 18 pages.
Statement of Grounds of Appeal, filed by Opponent Generics [UK] Ltd. on Jul. 8, 2019, further to the Notice of Appeal, filed on May 3, 2019, against the Interlocutory Decision, dated Feb. 28, 2019, in connection with the Opposition to European Patent No. 1 973 549 [D27=Seid et al. (2006) *Blood* 108(11):3739; D2a=U.S. Pat. No. 7,612,109; D1=U.S. Pat. No. 3,639,588; D3=Marchasin et al. (1964) *Blood* 23(3):354-358; D5=Preusser er al. (2005) *Clin. Expr. Pharmacol. Physiol.* 32:1020-1026; and D32=U.S. 2004/0180849], 11 pages.
Withdrawal of Appeal, filed by Opponent STADA Arzneimittel AG on Jul. 10, 2019, in connection with the Opposition to European Patent No. 1 973 549 [machine-generated English language translation and original document in German], 6 pages.
Statement of Grounds of Appeal, filed by Patent Proprietor Vifor (International) AG on Jul. 10, 2019, further to the Notice of Appeal, filed on May 10, 2019, against the Interlocutory Decision, dated Feb. 28, 2019, in connection with the Opposition to European Patent No. 1 973 549, 231 pages.
Communication pursuant to Article 94(3) EPC (Examination Report), dated May 24, 2019, in connectio with European Patent Application No. 16172826.6 [D3=WO 2004/037865; D8=MacDougall, I.C. (1999) *Kidney International* 55(69):S61-66; and D13=Fishbane, S. (2003) *Am. J. Kidney Dis*. 41(6 Suppl 5):S18-S26], 5 pages.
Order requiring a Statutory Disclaimer for claims 28 and 29 of U.S. Pat. No. 7,754,702, entered Aug. 23, 2019, in connection with PTAB Appeal No. IPR2015-01490, 4 pages.
Letter/Written Disclosure of the Supplemental Information Disclosure Statement for the above-referenced application, filed herewith on Aug. 23, 2019, 18 pages.
Patent Owner American Regent, Inc., Preliminary Response, filed Sep. 19, 2019, to the Petition of Pharmacosmos A/S, filed Jun. 14, 2019, in connection with U.S. Pat. No. 8,431,549 (Case No. IPR2019-01142), 29 pages.
Statement of Grounds and Particulars, dated Sep. 13, 2019, in support of the Notice of Opposition, filed Aug. 13, 2019 by Opponent Pharmacosmos Holding A/S, in connection with Austalian Patent Application No. 2016205002 [cited documents D1-D7 appended], 504 pages.
Correspondence, dated Sep. 16, 2019, from IP Australia Oppositions and Hearings, inquiring as to whether the parties wish to file evidence or request an oral hearing, in connection with the Opposition to Australian Patent Application No. 2016205002, 1 page.
Opponent Pharmacosmos Holding A/S's Intentions re Evidence and Request for Oral Hearing, dated Sep. 18, 2019, responsive to IP Australia's Correspondence of Sep. 16, 2019, in connection with Australia Patent Application No. 2016205002, 1 page.
Direction in the Opposition Proceedings, issued Oct. 2, 2019, by IP Australia, in connection with Australian Patent Application No. 2016205002, 1 page.
Response, filed Sep. 13, 2019, to Examiner's Report, dated Mar. 13, 2019, in connection with Canadian Patent Application No. 2,953,964, 253 pages.
Letter/Written Disclosure of the Supplemental Information Disclosure Statement for the above-referenced applications, filed herewith on Oct. 3, 2019, 4 pages.

\* cited by examiner

FIG. 1A - FIG. 1C
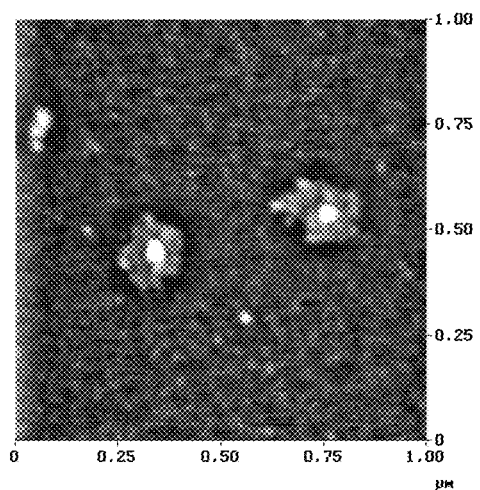
FIG. 1A
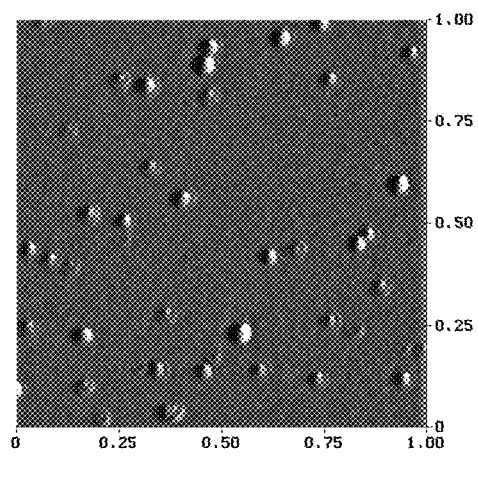
FIG. 1B
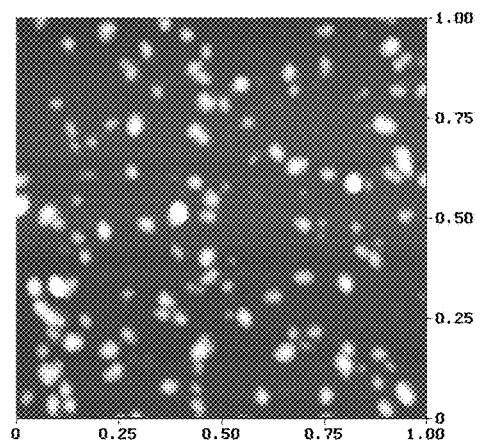
FIG. 1C

METHODS AND COMPOSITIONS FOR ADMINISTRATION OF IRON

CROSS-REFERENCE TO RELATED APPLICATIONS

This application is a Continuation application which claims priority to U.S. Non-Provisional application Ser. No. 13/847,254, filed 19 Mar. 2013; U.S. Non-Provisional application Ser. No. 12/787,283, filed 25 May 2010, issued as U.S. Pat. No. 8,431,549 on 30 Apr. 2013; and U.S. Non-Provisional application Ser. No. 11/620,986, filed 8 Jan. 2007, issued as U.S. Pat. No. 7,754,702 on 13 Jul. 2010; all of which claim priority to U.S. Provisional Application Ser. No. 60/757,119, filed 6 Jan. 2006; each of which is incorporated herein by reference in their entireties.

FIELD OF THE INVENTION

The present invention generally relates to treatment of iron-related conditions with iron carbohydrate complexes.

BACKGROUND

Parenteral iron therapy is known to be effective in a variety of diseases and conditions including, but not limited to, severe iron deficiency, iron deficiency anemia, problems of intestinal iron absorption, intestinal iron intolerance, cases where regular intake of an oral iron preparation is not guaranteed, iron deficiency where there is no response to oral therapy (e.g., dialysis patients), and situations where iron stores are scarcely or not at all formed but would be important for further therapy (e.g., in combination with erythropoietin). Geisser et al., Arzneimittelforschung (1992) 42(12), 1439-1452. There exist various commercially available parenteral iron formulations. But many currently available parenteral iron drugs, while purportedly effective at repleting iron stores, have health risks and dosage limitations associated with their use.

Currently available parenteral iron formulations approved for use in the U.S. include iron dextran (e.g., InFed, Dexferrum), sodium ferric gluconate complex in sucrose (Ferrlecit), and iron sucrose (Venofer). Although serious and life-threatening reactions occur most frequently with iron dextran, they are also known to occur with other parenteral iron products. In addition, non-life threatening reactions such as arthralgia, back pain, hypotension, fever, myalgia, pruritus, vertigo, and vomiting also occur. These reactions, while not life-threatening, often preclude further dosing and therefore iron repletion.

Iron dextran, the first parenteral iron product available in the United States (US), has been associated with an incidence of anaphylactoid-type reactions (i.e., dyspnea, wheezing, chest pain, hypotension, urticaria, angioedema). See generally Fishbane, Am J Kidney Dis (2003) 41(5Suppl), 18-26; Landry et al. (2005) Am J Nephrol 25, 400-410, 407. This high incidence of anaphylactoid reactions is believed to be caused by the formation of antibodies to the dextran moiety. Other parenteral iron products (e.g., iron sucrose and iron gluconate) do not contain the dextran moiety, and the incidence of anaphylaxis with these products is markedly lower. Fishbane, Am J Kidney Dis (2003) 41(5Suppl), 18-26; Geisser et al., Arzneimittelforschung (1992) 42(12), 1439-52. However, the physical characteristics of, for example, iron gluconate and iron sucrose lead to dosage and administration rate limitations. Negative characteristics include high pH, high osmolarity, low dosage limits (e.g., maximum 500 mg iron once per week, not exceeding 7 mg iron/kg body weight), and the long duration of administration (e.g., 100 mg iron over at least 5 minutes as an injection; 500 mg iron over at least 3.5 hours as a drip infusion). Furthermore, injectable high molecular mass substances produce more allergic reactions than the corresponding low molecular mass substances. Geisser et al. (1992) Arzneimittelforschung 42: 1439-1452.

Ferumoxytol is a newer parenteral iron formulation but limited information is available as to its efficacy and administration. See e.g., Landry et al. (2005) Am J Nephrol 25, 400-410, 408; and Spinowitz et al. (2005) Kidney Intl 68, 1801-1807; U.S. Pat. No. 6,599,498.

Various pharmacokinetic studies suggest that doses of iron complexes higher than 200 mg of iron are generally unsuitable and that the conventional therapy model prescribes repeated applications of lower doses over several days. See Geisser et al., (1992) Arzneimittelforschung 42: 1439-1452. For example, to achieve iron repletion under current therapy models, a total dose of 1 g typically requires 5 to 10 sessions over an extended period of time. These delivery modes incur significant expense for supplies such as tubing and infusate, costly nursing time, multiple administrations, and patient inconvenience.

SUMMARY OF THE INVENTION

Among the various aspects of the present invention is the provision of a method of treatment of iron-associated diseases, disorders, or conditions with iron formulations. Briefly, therefore, the present invention is directed to use of iron carbohydrate complexes that can be administered parenterally at relatively high single unit dosages, thereby providing a safe and efficient means for delivery of a total dose of iron in fewer sessions over the course of therapeutic treatment.

The present teachings include methods of treating a disease, disorder, or condition characterized by iron deficiency or dysfunctional iron metabolism through the administration of at least 0.6 grams of elemental iron via a single unit dosage of an iron carbohydrate complex to a subject that is in need of such therapy.

In various embodiments, the method treats anemia. In some embodiments, the anemia is an iron deficiency anemia, such as that associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidial anti-inflammatory agents, or chronic ingestion of erythropoiesis stimulating agents. In some aspects, the anemia is anemia of chronic disease, such as rheumatoid arthritis; cancer; Hodgkins leukemia; non-Hodgkins leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sojgren's syndrome; congestive heart failure/cardiomyopathy; or idiopathic geriatric anemia. In some embodiments, the anemia is due to impaired iron absorption or poor nutrition, such as anemia associated with Crohn's Disease; gastric surgery; ingestion of drug products that inhibit iron absorption; and chronic use of calcium. In various embodiments, the method treats restless leg syndrome; blood donation; Parkinson's disease; hair loss; or attention deficit disorder.

In various embodiments, the single dosage unit of elemental iron is between at least about 0.6 grams and 2.5 grams. In some embodiments, the single dosage unit of elemental iron is at least about 0.7 grams; at least about 0.8 grams; at least about 0.9 grams; at least about 1.0 grams; at least about 1.1 grams; at least about 1.2 grams; at least about 1.3 grams; at least about 1.4 grams; at least about 1.5 grams; at least about 1.6 grams; at least about 1.7 grams; at least about 1.8 grams; at least about 1.9 grams; at least about 2.0 grams; at least about 2.1 grams; at least about 2.2 grams; at least about 2.3 grams; at least about 2.4 grams; or at least about 2.5 grams.

In various embodiments, the single dosage unit of elemental iron is administered in about 15 minutes or less. In some embodiments, the single dosage unit of elemental iron is administered in about 10 minutes or less, about 5 minutes or less, or about 2 minutes or less.

In various embodiments, the subject does not experience a significant adverse reaction to the single dosage unit administration.

In various embodiments, the iron carbohydrate complex has a pH between about 5.0 to about 7.0; physiological osmolarity; an iron core size no greater than about 9 nm; a mean diameter particle size no greater than about 35 nm; a blood half-life of between about 10 hours to about 20 hours; a substantially non-immunogenic carbohydrate component; and substantially no cross reactivity with anti-dextran antibodies.

In various embodiments, the iron carbohydrate complex contains about 24% to about 32% elemental iron; contains about 25% to about 50% carbohydrate; has a molecular weight of about 90,000 daltons to about 800,000 daltons, or some combination thereof.

In various embodiments, the iron carbohydrate complex is an iron monosaccharide complex, an iron disaccharide complex, or an iron polysaccharide complex. In some embodiments, the iron carbohydrate complex is iron carboxymaltose complex, iron mannitol complex, iron polyisomaltose complex, iron polymaltose complex, iron gluconate complex, iron sorbitol complex, or an iron hydrogenated dextran complex. In some embodiments, the iron carbohydrate complex is an iron polyglucose sorbitol carboxymethyl ether complex. In some preferred embodiments, the iron carboxymaltose complex contains about 24% to about 32% elemental iron, about 25% to about 50% carbohydrate, and is about 100,000 daltons to about 350,000 daltons. In some preferred embodiments, the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between 5 and 20, and when a mixture of several maltodextrins is applied, the dextrose equivalent lies between 5 and 20 and the dextrose equivalent of each individual maltodextrin contained in the mixture lies between 2 and 20. In some preferred embodiments, the iron carboxymaltose complex has a chemical formula of $[FeO_x(OH)_y(H_2O)_z]_n[\{(C_6H_{10}O_5)_m(C_6H_{12}O_7)\}_l]_k$, where n is about 103, m is about 8, l is about 11, and k is about 4; contains about 28% elemental iron; and has a molecular weight of about 150,000 Da. In some preferred embodiments, the iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate.

In various embodiments, the iron carbohydrate complex comprises an iron core with a mean iron core size of no greater than about 9 nm. In some embodiments, the mean iron core size is at least about 1 nm but no greater than about 9 nm; at least about 3 nm but no greater than about 7 nm; or at least about 4 nm but not greater than about 5 nm.

In various embodiments, the mean size of a particle of the iron carbohydrate complex is no greater than about 35 nm. In some embodiments, the particle mean size is no greater than about 30 nm. In some embodiments, the particle mean size is no greater than about 25 nm. In some embodiments, the particle mean size is no greater than about 20 nm; no greater than about 15 nm; no greater than about 10 nm; or at least about 6 nm but no greater than about 7 nm.

In various embodiments, the iron carbohydrate complex is administered parenterally, for example intravenously or intramuscularly. In some embodiments, the iron carbohydrate complex is intravenously infused. In certain embodiments, the single unit dose of iron carbohydrate complex is intravenously infused at a concentration of about 1000 mg elemental iron in about 200 ml to about 300 ml of diluent, for example, about 250 ml of diluent or about 215 ml of diluent. In some embodiments, the iron carbohydrate complex is intravenously injected as a bolus. In certain embodiments, the iron carbohydrate complex is intravenously injected as a bolus at a concentration of about 1000 mg elemental iron in about 200 ml to about 300 ml of diluent, for example, about 250 ml of diluent or about 215 ml of diluent. In some embodiments, the iron carbohydrate complex is intramuscularly infused at a concentration of about 1000 mg elemental iron in about 200 ml to about 300 ml of diluent, for example, about 250 ml of diluent or about 215 ml of diluent. In some embodiments, the iron carbohydrate complex is intramuscularly infused at a concentration of about 500 mg elemental iron in less than about 10 ml diluent.

In various embodiments, the method also includes a second administration of the iron carbohydrate complex upon recurrence of at least one symptom of the treated disease, disorder, or condition.

In various embodiments, the method also includes a second administration of the iron carbohydrate complex after 1 day to 12 months after the first administration.

In a preferred embodiment, the method of treating a disease, disorder, or condition characterized by iron deficiency or dysfunctional iron metabolism comprises intravenously administering to a subject in need thereof an iron carboxymaltose complex in a single dosage unit of at least about 1000 mg of elemental iron in about 200 ml to about 300 ml of diluent in about 5 minutes or less; wherein the iron carboxymaltose complex comprises an iron core with a mean iron core size of at least about 1 nm but no greater than about 9 nm; mean size of a particle of the iron carboxymaltose complex is no greater than about 35 nm; and the iron carboxymaltose complex is administered intravenously infused or intravenously injected at a concentration of about 1000 mg elemental iron in about 200 ml to about 300 ml of diluent. In some these embodiments, the iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate. In some these embodiments, the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between about 5 and about 20, and when a mixture of several maltodextrins is applied, the dextrose equivalent lies between about 5 and about 20 and the dextrose equivalent of each individual maltodextrin contained in the mixture lies between about 2 and about 20.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A-FIG. 1C are a series of electron micrographs that depict the particle size of three iron carbohydrate complexes. FIG. 1A is an electron micrograph depicting the particle size of Dexferrum (an iron dextran). FIG. 1B is an electron micrograph depicting the particle size of Venofer (an iron sucrose). FIG. 1C is an electron micrograph depicting the particle size of polynuclear iron (III)-hydroxide 4(R)-(poly-(1→4)-O-α-glucopyranosyl)-oxy-2(R),3(S),5(R),6-tetrahydroxy-hexanoate ("VIT-45", an iron carboxymaltose complex).

DETAILED DESCRIPTION OF THE INVENTION

Figure 2:
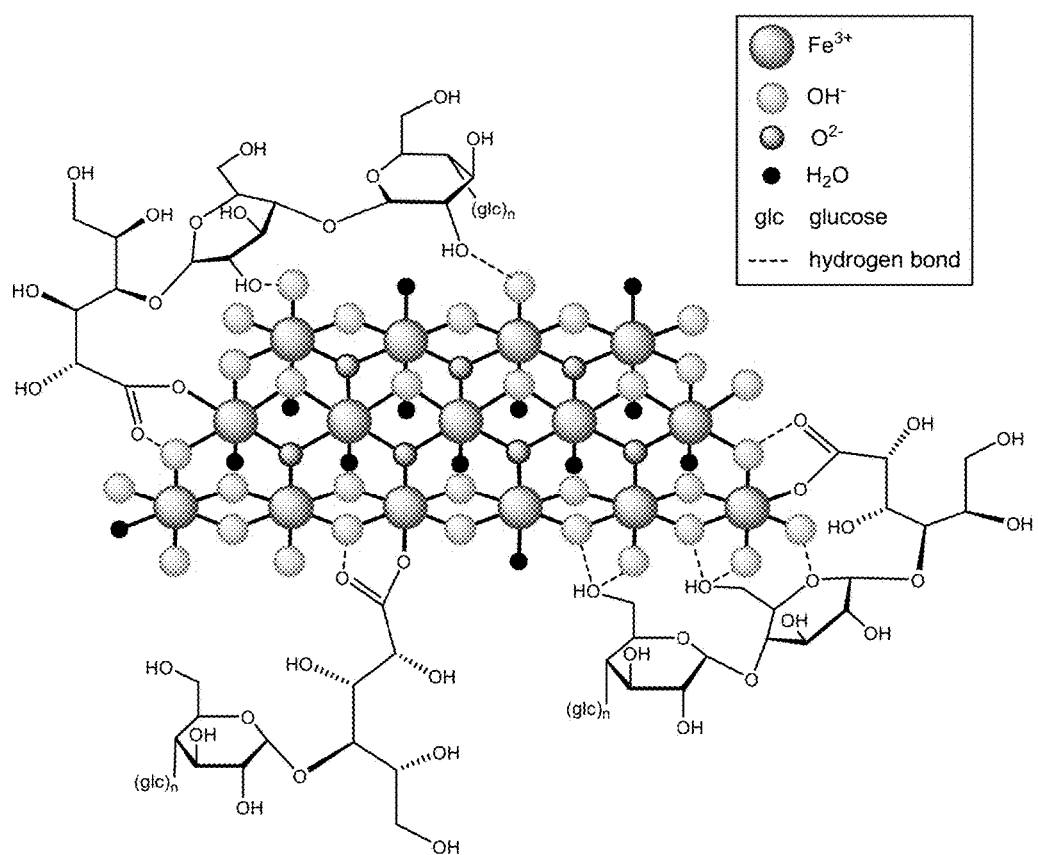
FIG. 2 is a schematic representation of an exemplary iron carboxymaltose complex.

The present invention makes use of iron carbohydrate complexes that can be administered parenterally at relatively high single unit dosages for the therapeutic treatment of a variety of iron-associated diseases, disorders, or conditions. Generally, states indicative of a need for therapy with high single unit dosages of iron carbohydrate complexes include, but are not limited to iron deficiency anemia, anemia of chronic disease, and states characterized by dysfunctional iron metabolism. Efficacious treatment of these, and other, diseases and conditions with parenteral iron formulations (supplied at lower single unit dosages than those described herein) is generally known in the art. See e.g., Van Wyck et al. (2004) J Am Soc Nephrol 15, S91-S92. The present invention is directed to use of iron carbohydrate complexes that can be administered parenterally at relatively high single unit dosages, thereby providing a safe and efficient means for delivery of a total dose of iron in fewer sessions over the course of therapeutic treatment.

Iron deficiency anemia is associated with, for example, chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidial anti-inflammatory agents, or chronic ingestion of erythropoiesis stimulating agents.

Anemia of chronic disease is associated with, for example, rheumatoid arthritis; cancer; Hodgkins leukemia; non-Hodgkins leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sojgren's syndrome; congestive heart failure/cardiomyopathy; and idiopathic geriatric anemia.

Anemia is also associated with, for example, Crohn's Disease; gastric surgery; ingestion of drug products that inhibit iron absorption; and chronic use of calcium.

States characterized by dysfunctional iron metabolism and treatable with the single unit dosages of iron carbohydrate complexes described herein include, but are not limited to, restless leg syndrome; blood donation; Parkinson's disease; hair loss; and attention deficit disorder.

Again, each of the above listed states, diseases, disorders, and conditions, as well as others, can benefit from the treatment methodologies described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms.

The benefit to a subject to be treated is either statistically significant or at least perceptible to the patient or to the physician. Measures of efficacy of iron replacement therapy are generally based on measurement of iron-related parameters in blood. The aim of treatment is usually to return both Hb and iron stores to normal levels. Thus, efficacy of iron replacement therapy can be interpreted in terms of the ability to normalise Hb levels and iron stores. The effectiveness of treatment with one or more single unit doses of iron carbohydrate complex, as described herein, can be demonstrated, for example, by improvements in ferritin and transferrin saturation, and in raising hemoglobin levels in anemic patients. Iron stores can be assessed by interpreting serum ferritin levels. TfS is frequently used, in addition, to diagnose absolute or functional iron deficiencies. In patients with iron deficiency, serum transferrin is elevated and will decrease following successful iron treatment.

Administration

Methods of treatment of various diseases, disorders, or conditions with iron complex compositions comprise the administration of the complex in single unit dosages of at least 0.6 grams of elemental iron to about at least 2.5 grams of elemental iron. Administration of single unit dosages can be, for example, over pre-determined time intervals or in response to the appearance and/or reappearance of symptoms. For example, the iron carbohydrate complex can be re-administered upon recurrence of at least one symptom of the disease or disorder. As another example, the iron carbohydrate complex can be re-administered at some time period after the initial administration (e.g., after 4 days to 12 months).

Any route of delivery of the single unit dose of iron carbohydrate complex is acceptable so long as iron from the iron complex is released such that symptoms are treated. The single unit dose of iron carbohydrate complex can be administered parenterally, for example intravenously or intramuscularly. Intravenous administration can be delivered as a bolus or preferably as an infusion. For example, the single unit dose of iron carbohydrate complex can be intravenously infused at a concentration of about 1000 mg elemental iron in about 200 ml to about 300 ml of diluent, preferably about 215 ml of diluent or about 250 ml of diluent. The iron carbohydrate complex can be intravenously injected as a bolus. For example, the iron carbohydrate complex can be intravenously injected as a bolus at a concentration of about 1000 mg elemental iron in about 200 ml to about 300 ml of diluent, preferably about 215 ml of diluent or about 250 ml of diluent. The iron carbohydrate complex can be intramuscularly infused at a concentration of, for example, about 1000 mg elemental iron in about 200 ml to about 300 ml of diluent, preferably, about 250 ml of diluent or about 215 ml of diluent. If applied as an infusion, the iron carbohydrate complex can be diluted with sterile saline (e.g., polynuclear iron (III)-hydroxide 4(R)-(poly-(1→4)-O-α-glucopyranosyl)-oxy-2(R),3(S),5(R),6-tetrahydroxy-hexanoate ("VIT-45") 0.9% m/V NaCl or 500 mg iron in up to 250 mL NaCl). The iron carbohydrate complex can be intravenously injected as a bolus without dilution. As an example, the iron carbohydrate complex can be intramuscularly injected at a concentration of about 500 mg elemental iron in less than about 10 ml diluent, preferably about 5 ml.

Generally, total iron dosage will depend on the iron deficit of the patient. One skilled in the art can tailor the total iron dose required for a subject while avoiding iron overload, as overdosing with respect to the total required amount of iron has to be avoided, as is the case for all iron preparations.

The total iron dosage can be delivered as a single unit dosage or a series of single unit dosages. An appropriate single unit dosage level will generally be at least 0.6 grams of elemental iron, particularly at least 0.7 grams; at least 0.8 grams; at least 0.9 grams; at least 1.0 grams; at least 1.1 grams; at least 1.2 grams; at least 1.3 grams; at least 1.4 grams; at least 1.5 grams; at least 1.6 grams; at least 1.7 grams; at least 1.8 grams; at least 1.9 grams; at least 2.0 grams; at least 2.1 grams; at least 2.2 grams; at least 2.3 grams; at least 2.4 grams; or at least 2.5 grams. For example, a single unit dosage is at least 1.0 grams of elemental iron. As another example, a single unit dosage is at least 1.5 grams of elemental iron. As a further example, a single unit dosage is at least 2.0 grams of elemental iron. In yet another example, a single unit dosage is at least 2.5 grams of elemental iron.

An appropriate single unit dosage level can also be determined on the basis of patient weight. For example, an appropriate single unit dosage level will generally be at least 9 mg of elemental iron per kg body weight, particularly at least 10.5 mg/kg, at least 12 mg/kg, at least 13.5 mg/kg, at least 15 mg/kg, at least 16.5 mg/kg, at least 18 mg/kg, at least 19.5 mg/kg, at least 21 mg/kg, at least 22.5 mg/kg, at least 24 mg/kg, at least 25.5 mg/kg, at least 27 mg/kg, at least 28.5 mg/kg, at least 30 mg/kg, at least 31.5 mg/kg, at least 33 mg/kg, at least 34.5 mg/kg, at least 36 mg/kg, or at least 37.5 mg/kg.

Preferably, a single unit dosage can be administered in 15 minutes or less. For example, the single unit dosage can be administered in 14 minutes or less, 13 minutes or less, 12 minutes or less, 11 minutes or less, 10 minutes or less, 9 minutes or less, 8 minutes or less, 7 minutes or less, 6 minutes or less, 5 minutes or less, 4 minutes or less, 3 minutes or less, or 2 minutes or less.

Administration of iron can occur as a one-time delivery of a single unit dose or over a course of treatment involving delivery of multiple single unit doses. Multiple single unit doses can be administered, for example, over pre-determined time intervals or in response to the appearance and reappearance of symptoms. The frequency of dosing depends on the disease or disorder being treated, the response of each individual patient, and the administered amount of elemental iron. An appropriate regime of dosing adequate to allow the body to absorb the iron from the bloodstream can be, for example, a course of therapy once every day to once every eighteen months.

Such consecutive single unit dosing can be designed to deliver a relatively high total dosage of iron over a relatively low period of time. For example, a single unit dose (e.g., 1000 mg) can be administered every 24 hours. As illustration, a total dose of 2000, 2500, 3000, 3500, 4000, 4500, or 5000 mg of elemental iron can be delivered via consecutive daily single unit doses of about 600 mg to about 1000 mg of elemental iron. Given that a single unit dose of 1000 mg can be intravenously introduced into a patient in a concentrated form over, for example, two minutes, such administrative protocol provides a practitioner and patient with an effective, efficient, and safe means to deliver elemental iron.

As another example, a single unit dose can be administered every 3-4 days. As a further example, a single unit dose can be administered once per week. Alternatively, the single unit doses of iron complex may be administered ad hoc, that is, as symptoms reappear, as long as safety precautions are regarded as practiced by medical professionals.

It will be understood, however, that the specific dose and frequency of administration for any particular patient may be varied and depends upon a variety of factors, including the activity of the employed iron complex, the metabolic stability and length of action of that complex, the age, body weight, general health, sex, diet, mode and time of administration, rate of excretion, drug combination, the severity and nature of the particular condition, and the host undergoing therapy.

The following provides but a few examples of treatment protocols for various diseases or disorders.

Iron carbohydrate complex can be given as a single unit dose for the treatment of Restless Leg Syndrome. For example, 1000 mg of elemental iron from an iron carboxymaltose (e.g., polynuclear iron (III)-hydroxide 4(R)-(poly-(1→4)-O-α-glucopyranosyl)-oxy-2(R),3(S),5(R),6-tetrahydroxy-hexanoate) can be intravenously injected as a single dose (e.g., 1.5-5 mg iron/ml in normal saline) to a subject suffering from Restless Leg Syndrome. A single intravenous treatment can provide relief of symptoms for an extended period of time, approximately two to twelve monthscitcit_af ref_bf(Nordlander, 1953 ref_num37)ref_af, although relief may be granted for shorter or longer periods. See U.S. Patent Pub. No. 2004/0180849, incorporated herein by reference. If desired, post-infusion changes in central nervous system iron status can be monitored using measurements of cerebral spinal fluid (CSF) ferritin (and other iron-related proteins) and of brain iron stores using MRI. Post-infusion changes in Restless Leg Syndrome are assessed using standard subjective (e.g., patient diary, rating scale) and objective (e.g., P50, SIT, Leg Activity Meters) measures of clinical status. If desired, to better evaluate RLS symptom amelioration, CSF and serum iron values, MRI measures of brain iron and full clinical evaluations with sleep and immobilization tests are obtained prior to treatment, approximately two weeks after treatment, and again twelve months later or when symptoms return. Clinical ratings, Leg Activity Meter recordings and serum ferritin are obtained monthly after treatment. CSF ferritin changes can also be used to assess symptom dissipation.

Iron carbohydrate complex can be given as a single unit dose for the treatment of iron deficiency anemia secondary to heavy uterine bleeding. For example, a single unit dose of 1,000 mg of elemental iron from an iron carboxymaltose in about 250 cc normal saline can be intravenously injected into a subject suffering from iron deficiency anemia secondary to heavy uterine bleeding over 15 minutes every week until a calculated iron deficit dose has been administered. The iron deficit dose can be calculated as follows:

If baseline TSAT <20% or Baseline Ferritin <50 ng/ml: Dose=Baseline weight (kg)×(15-Baseline Hgb [g/dL])×2.4+500 mg

OR

If baseline TSAT >20% and Baseline Ferritin >50 ng/mL: Dose=Baseline weight (kg)×(15-Baseline Hgb [g/dL])×2.4

(NOTE: Baseline Hgb equals the average of the last two central lab Hgb's)

Iron carbohydrate complex can be given as a single unit dose for the treatment of iron deficiency anemia. A subject diagnosed as suffering from iron deficiency anemia can be, for example, intravenously injected with a dose of 1,000 mg of iron as VIT-45 (or 15 mg/kg for weight <66 kg) in 250 cc of normal saline over 15 minutes. Subjects with iron deficiency anemia secondary to dialysis or non-dialysis dependent-Chronic Kidney Disease (CKD) as per K/DOQI guidelines will generally have Hgb <12 g/dL; TSAT <25%; and Ferritin <300 ng/mL. Subjects with iron deficiency anemia secondary to Inflammatory Bowel Disease will generally have Hgb <12 g/dL; TSAT <25%; and Ferritin <300 ng/mL. Subjects with iron deficiency anemia secondary to other conditions will generally have Hgb <12 g/dL; TSAT <25%; and Ferritin <100 ng/mL.

Subject in Need Thereof

Single unit dosages of intravenous iron described herein can be administered to a subject where there is a clinical need to deliver iron rapidly or in higher doses and/or in subjects with functional iron deficiency such as those on erythropoietin therapy. A determination of the need for treatment with parenteral iron is within the abilities of one skilled in the art. For example, need can be assessed by monitoring a patient's iron status. The diagnosis of iron deficiency can be based on appropriate laboratory tests, for example, haemoglobin (Hb), serum ferritin, serum iron, transferrin saturation (TfS), and hypochromic red cells.

A determination of the need for treatment with high dosages of parenteral iron can be also be determined through diagnosis of a patient as suffering from a disease, disorder, or condition that is associated with iron deficiency or dysfunctional iron metabolism. For example, many chronic renal failure patients receiving erythropoietin will require intravenous iron to maintain target iron levels. As another example, most hemodialysis patients will require repeated intravenous iron administration, due to dialysis-associated blood loss and resulting negative iron balance.

Monitoring frequency can depend upon the disease, disorder, or condition the patient is afflicted with or at risk for. For example, in a patient initiating erythropoietin therapy, iron indices are monitored monthly. As another example, in patients who have achieved target range Hb or are receiving intravenous iron therapy, TSAT and ferritin levels can be monitored every 3 months.

A patient's iron status can be indicative of an absolute or a functional iron deficiency, both of which can be treated with the compositions and methods described herein. An absolute iron deficiency occurs when an insufficient amount of iron is available to meet the body's requirements. The insufficiency may be due to inadequate iron intake, reduced bioavailability of dietary iron, increased utilization of iron, or chronic blood loss. Prolonged iron deficiency can lead to iron deficiency anemia—a microcytic, hypochromic anemia in which there are inadequate iron stores. Absolute iron deficiency is generally indicated where TSAT <20% and Ferritin <100 ng/mL.

Functional iron deficiency can occur where there is a failure to release iron rapidly enough to keep pace with the demands of the bone marrow for erythropoiesis, despite adequate total body iron stores. In these cases, ferritin levels may be normal or high, but the supply of iron to the erythron is limited, as shown by a low transferrin saturation and an increased number of microcytic, hypochromic erythrocytes. Functional iron deficiency can be characterized by the following characteristics: Inadequate hemoglobin response to erythropoietin; Serum ferritin may be normal or high; Transferrin saturation (TSAT) usually <20%; and/or reduced mean corpuscular volume (MCV) or mean corpuscular hemoglobin concentration (MCHC) in severe cases. Functional iron deficiency (i.e., iron stores are thought to be adequate but unavailable for iron delivery) is generally indicated where TSAT <20% and Ferritin >100 ng/mL.

Assessing the need for intravenous iron therapy as described herein can be according to the National Kidney Foundation's Kidney Disease Outcomes Quality Initiative. See NKF-K/DOQI, Clinical Practice Guidelines for Anemia of Chronic Kidney Disease (2000); Am J Kidney Dis (2001) 37(supp 1), S182-S238. The DOQI provides optimal clinical practices for the treatment of anemia in chronic renal failure. The DOQI guidelines specify intravenous iron treatment of kidney disease based on hemoglobin, transferrin saturation (TSAT), and ferritin levels.

Assessment of need for intravenous iron therapy can also be according to a patient's target iron level. For example, the target hemoglobin level of a patient can be selected as 11.0 g/dL to 12.0 g/dL (hematocrit approximately 33% to 36%). To achieve target hemoglobin with optimum erythropoietin doses, sufficient iron, supplied via an iron carbohydrate complex, is provided to maintain TSAT ≥20% and ferritin ≥100 ng/mL. In erythropoietin-treated patients, if TSAT levels are below 20%, the likelihood that hemoglobin will rise or erythropoietin doses fall after iron administration is high. Achievement of target hemoglobin levels with optimum erythropoietin doses is associated with providing sufficient iron to maintain TSAT above 20%.

Iron therapy can be given to maintain target hemoglobin while preventing iron deficiency and also preventing iron overload. Adjusting dosage of iron to maintain target levels of hemoglobin, hematocrit, and laboratory parameters of iron storage is within the normal skill in the art. For example, where a patient is anemic or iron deficient, intravenous iron can be administered when a patient has a ferritin <800, a TSAT <50, and/or a Hemoglobin <12. Iron overload can be avoided by withholding iron for TSAT >50% and/or ferritin >800 ng/m L.

Where a patient is not anemic or iron deficient but is in need of iron administration, for example a patient suffering from Restless Leg Syndrome, hemoglobin and TSAT levels are not necessarily relevant, while ferritin >800 can still provides a general cut off point for administration.

Iron Carbohydrate Complex

Iron carbohydrate complexes are commercially available, or have well known syntheses. Examples of iron carbohydrate complexes include iron monosaccharide complexes, iron disaccharide complexes, iron oligosaccharide complexes, and iron polysaccharide complexes, such as: iron carboxymaltose, iron sucrose, iron polyisomaltose, iron polymaltose, iron gluconate, iron sorbitol, iron hydrogenated dextran, which may be further complexed with other compounds, such as sorbitol, citric acid and gluconic acid (for example iron dextrin-sorbitol-citric acid complex and iron sucrose-gluconic acid complex), and mixtures thereof.

Applicants have discovered that certain characteristics of iron carbohydrate complexes make them amenable to administration at dosages far higher than contemplated by current administration protocols. Preferably, iron carbohydrate complexes for use in the methods described herein are those which have one or more of the following characteristics: a nearly neutral pH (e.g., about 5 to about 7); physiological osmolarity; stable carbohydrate component; an iron core size no greater than about 9 nm; mean diameter particle size no greater than about 35 nm, preferably about 25 nm to about 30 nm; slow and competitive delivery of the complexed iron to endogenous iron binding sites; serum half-life of over about 7 hours; low toxicity; non-immunogenic carbohydrate component; no cross reactivity with anti-dextran antibodies; and/or low risk of anaphylactoid/hypersensitivity reactions.

It is within the skill of the art to test various characteristics of iron carbohydrate complexes as so determine amenability to use in the methods described herein. For example, pH and osmolarity are straightforward determinations performed on a sample formulation. Likewise, techniques such as electron micrograph imaging, transmission electron microscopy, and atomic force microscopy provide direct methods to analyze both iron core and particle size. See e.g., FIG. 1; Table 1. The stability of the carbohydrate complex can be assessed through physicochemical properties such as kinetic characteristics, thermodynamic characteristics, and degradation kinetics. See Geisser et al., Arzneimittelforschung (1992) 42(12), 1439-1452. Useful techniques to assess physical and electronic properties include absorption spectroscopy, X-ray diffraction analysis, transmission electron microscopy, atomic force microscopy, and elemental analysis. See Kudasheva et al. (2004) J Inorg Biochem 98, 1757-1769. Pharmacokinetics can be assessed, for example, by iron tracer experiments. Hypersensitivity reactions can be monitored and assessed as described in, for example, Bailie et al. (2005) Nephrol Dial Transplant, 20(7), 1443-1449. Safety, efficacy, and toxicity in human subjects can be assessed, for example, as described in Spinowitz et al. (2005) Kidney Intl 68, 1801-1807.

A particularly preferred iron carbohydrate complex will have a pH between 5.0-7.0; physiological osmolarity; an iron core size no greater than 9 nm; mean diameter particle size no greater than 30 nm; serum half-life of over 10 hours; a non-immunogenic carbohydrate component; and no cross reactivity with anti-dextran antibodies. One example of a preferred iron carbohydrate complex for use in the methods described herein is an iron carboxy-maltose complex (e.g., polynuclear iron (III)-hydroxide 4(R)-(poly-(1→4)-O-α-glucopyranosyl)-oxy-2(R),3(S),5(R),6-tetrahydroxy-hexanoate, "VIT-45"). Another example of a preferred iron carbohydrate complex for use in the methods described herein is a carboxyalkylated reduced polysaccharide iron oxide complex (e.g., ferumoxytol, described in U.S. Pat. No. 6,599,498).

Preferably, an iron carbohydrate complex, for use in methods disclosed herein, contains about 24% to about 32% elemental iron, more preferably about 28% elemental iron. Preferably, an iron carbohydrate complex, for use in methods disclosed herein, contains about 25% to about 50% carbohydrate (e.g., total glucose). Preferably, an iron carbohydrate complex, for use in methods disclosed herein, is about 90,000 daltons to about 800,000 daltons, more preferably 100,000 daltons to about 350,000 daltons.

Iron Carboxymaltose Complex

One preferred iron carbohydrate complex for use in the methods described herein is an iron carboxymaltose complex. An example of an iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate ("VIT-45"). VIT-45 is a Type I polynuclear iron (III) hydroxide carbohydrate complex that can be administered as parenteral iron replacement therapy for the treatment of various anemia-related conditions as well as other iron-metabolism related conditions. VIT-45 can be represented by the chemical formula: $[FeOx(OH)y(H2O)z]n[\{(C6H10O5)m(C6H12O7)\}l]k$, where n is about 103, m is about 8, l is about 11, and k is about 4). The molecular weight of VIT-45 is about 150,000 Da. An exemplary depiction of VIT-45 is provided in FIG. 2.

The degradation rate and physicochemical characteristics of the iron carbohydrate complex (e.g., VIT-45) make it an efficient means of parenteral iron delivery to the body stores. It is more efficient and less toxic than the lower molecular weight complexes such as iron sorbitol/citrate complex, and does not have the same limitations of high pH and osmolarity that leads to dosage and administration rate limitations in the case of, for example, iron sucrose and iron gluconate.

The iron carboxymaltose complex (e.g., VIT-45) generally does not contain dextran and does not react with dextran antibodies; therefore, the risk of anaphylactoid/hypersensitivity reactions is very low compared to iron dextran. The iron carboxymaltose complex (e.g., VIT-45) has a nearly neutral pH (5.0 to 7.0) and physiological osmolarity, which makes it possible to administer higher single unit doses over shorter time periods than other iron-carbohydrate complexes. The iron carboxymaltose complex (e.g., VIT-45) can mimic physiologically occurring ferritin. The carbohydrate moiety of iron carboxymaltose complex (e.g., VIT-45) is metabolized by the glycolytic pathway. Like iron dextran, the iron carboxymaltose complex (e.g., VIT-45) is more stable than iron gluconate and sucrose. The iron carboxymaltose complex (e.g., VIT-45) produces a slow and competitive delivery of the complexed iron to endogenous iron binding sites resulting in an acute toxicity one-fifth that of iron sucrose. These characteristics of the iron carboxymaltose complex (e.g., VIT-45) allow administration of higher single unit doses over shorter periods of time than, for example, iron gluconate or iron sucrose. Higher single unit doses can result in the need for fewer injections to replete iron stores, and consequently is often better suited for outpatient use.

After intravenous administration, the iron carboxymaltose complex (e.g., VIT-45) is mainly found in the liver, spleen, and bone marrow. Pharmacokinetic studies using positron emission tomography have demonstrated a fast initial elimination of radioactively labeled iron $(Fe)^{52}Fe/^{59}Fe$ VIT-45 from the blood, with rapid transfer to the bone marrow and rapid deposition in the liver and spleen. See e.g., Beshara et al. (2003) Br J Haematol 2003; 120(5): 853-859. Eight hours after administration, 5 to 20% of the injected amount was observed to be still in the blood, compared with 2 to 13% for iron sucrose. The projected calculated terminal half-life $(t_{1/2})$ was approximately 16 hours, compared to 3 to 4 days for iron dextran and 6 hours for iron sucrose.

The iron in the iron carboxymaltose complex (e.g., VIT-45) slowly dissociates from the complex and can be efficiently used in the bone marrow for Hgb synthesis. Under VIT-45 administration, red cell utilization, followed for 4 weeks, ranged from 61% to 99%. Despite the relatively higher uptake by the bone marrow, there was no saturation of marrow transport systems. Thus, high red cell utilization of iron carboxymaltose complex occurs in anemic patients. In addition, the reticuloendothelial uptake of this complex reflects the safety of polysaccharide complexes. Non-saturation of transport systems to the bone marrow indicated the presence of a large interstitial transport pool (e.g., transferrin).

Other studies in patients with iron deficiency anemia revealed increases in exposure roughly proportional with VIT-45 dose (maximal total serum iron concentration was approximately 150 μg/mL and 320 μg/mL following 500 mg and 1000 mg doses, respectively). In these studies, VIT-45 demonstrated a monoexponential elimination pattern with a $t_{1/2}$ in the range 7 to 18 hours, with negligible renal elimination.

Single-dose toxicity studies have demonstrated safety and tolerance in rodents and dogs of intravenous doses of an iron carboxymaltose complex (VIT-45) up to 60 times more than the equivalent of an intravenous infusion of 1,000 mg iron once weekly in humans. Pre-clinical studies in dogs and rats administered VIT-45 in cumulative doses up to 117 mg iron/kg body weight over 13 weeks showed no observed adverse effect level in dose-related clinical signs of iron accumulation in the liver, spleen, and kidneys. No treatment-related local tissue irritation was observed in intra-arterial, perivenous, or intravenous tolerance studies in the rabbit. In vitro and in vivo mutagenicity tests provided no evidence that VIT-45 is clastogenic, mutagenic, or causes chromosomal damage or bone marrow cell toxicity. There were no specific responses to VIT-45 in a dextran antigenicity test.

Approximately 1700 subjects have been treated with an iron carboxymaltose complex (VIT-45) in open label clinical trials (see e.g., Example 5). Many of these subjects have received at least one dose of 15 mg/kg (up to a maximum dose of 1,000 mg) of VIT-45 over 15 minutes intravenously. Few adverse events and no serious adverse events or withdrawals due to adverse events related to VIT-45 administration have been reported. No clinically relevant adverse changes in safety laboratories have been seen.

The physicochemical characteristics of the iron carboxymaltose complex (e.g., VIT-45), the pattern of iron deposition, and the results of the above described studies demonstrate that iron carboxymaltose complex can be safely administered at high single unit therapeutic doses as described herein.

Polyglucose Sorbitol Carboxymethyl Ether-coated Non-stoichiometric Magnetite

Another preferred iron carbohydrate complex for use in the methods described herein is a polyglucose sorbitol carboxymethyl ether-coated non-stoichiometric magnetite (e.g., "ferumoxytol"). Ferumoxytol is known in the art to be effective for treating anemia (at single unit doses lower than described herein). See e.g., Spinowitz et al. (2005) Kidney Intl 68, 1801-1807. Ferumoxytol is a superparamagnetic iron oxide that is coated with a low molecular weight semi-synthetic carbohydrate, polyglucose sorbitol carboxymethyl ether. Ferumoxytol and its synthesis are described in U.S. Pat. No. 6,599,498, incorporated herein by reference. Safety, efficacy, and pharmacokinetics of ferumoxytol are as described, for example, in Landry et al. (2005) Am J Nephrol 25, 400-410, 408; and Spinowitz et al. (2005) Kidney Intl 68, 1801-1807.

The iron oxide of ferumoxytol is a superparamagnetic form of non-stoichiometric magnetite with a crystal size of 6.2 to 7.3 nm. Average colloidal particle size can be about 30 nm, as determined by light scattering. Molecular weight is approximately 750 kD. The osmolarity of ferumoxytol is isotonic at 297 mOsm/kg and the pH is neutral. The blood half-life of ferumoxytol is approximately 10-14 hours. It has been previously reported that ferumoxytol can be given by direct intravenous push over 1-5 minutes in doses up to 1,800 mg elemental iron per minute, with maximal total dose up to 420 mg per injection. Landry et al. (2005) Am J Nephrol 25, 400-410, 408.

Core and Particle Size

Intravenous iron agents are generally spheroidal iron-carbohydrate nanoparticles. At the core of each particle is an iron-oxyhydroxide gel. The core is surrounded by a shell of carbohydrate that stabilizes the iron-oxyhydroxide, slows the release of bioactive iron, and maintains the resulting particles in colloidal suspension. Iron agents generally share the same core chemistry but differ from each other by the size of the core and the identity and the density of the surrounding carbohydrate. See Table 1; FIG. 1.

TABLE 1

Core and Particle Size of Iron Carbohydrate Complexes

| | Iron (III) Control Release Test | Size of the Particle (nm) +/− SEM | |
| --- | --- | --- | --- |
| | $T_{75}$ (min) | Iron core | Total Particle |
| Dexferrum (an iron dextran) | 122.5 | 11.8 ± 4 | 27 ± 6 |
| VIT-45 (an iron carboxymaltose) | 117.8 | 4.4 ± 1.4 | 6.7 ± 2.5 |
| Venofer (an iron sucrose) | 10.2 | 2.8 ± 1 | 6.5 ± 4 |

Differences in core size and carbohydrate chemistry can determine pharmacological and biological differences, including clearance rate after injection, iron release rate in vitro, early evidence of iron bioactivity in vivo, and maximum tolerated dose and rate of infusion.

One of the primary determinants of iron bioactivity is the size of the core and the surface area to volume ratio. Generally, the rate of labile iron release in each agent is inversely related to the size of its iron core. Van Wyck (2004) J. Am. Soc. Nephrology 15, S107-S111, S109. Furthermore, in vitro iron donation to transferrin is inversely related to core size. Core size can depend upon the number of iron atoms contained within. For example, the number of iron atoms contained within a 1 nm core is calculated to be 13, while a 10 nm core is calculated to contain 12770 iron atoms. Where agents share the same core chemistry, the rate of iron release per unit surface area is likely similar, differing perhaps by the strength of the carbohydrate ligand-core iron bound. But for the same total amount of core iron, surface area available for iron release increases dramatically as core radius decreases. That is to say, for equal amounts of iron, the smaller the core, the greater the surface area available for iron release. Of course, the explanation for this non-linear trend is the fact that volume is radius cubed. In short, a collection of many small spheres exposes a greater total surface area than does a collection of an equal mass of fewer, larger spheres.

A smaller iron core size of an iron complex administered for the treatment of various diseases, disorders, or conditions allows wider distribution through tissues, a greater rate of labile iron release, and increased in vitro iron donation to transferrin. Furthermore, the iron complex is more evenly distributed and metabolizes faster due to the smaller core size. But if the core size is too small, the iron complex can move into cells unable to metabolize iron. In one embodiment, an iron complex with a mean iron core size of no greater than about 9 nm is administered. In various embodiments, mean iron core size is less than about 9 nm but greater than about 1 nm, about 2 nm, about 3 nm, about 4 nm, about 5 nm, about 6 nm, about 7 nm, or about 8 nm. Mean iron core size can be, for example, between about 1 nm and about 9 nm; between about 3 nm and about 7 nm; or between about 4 nm and about 5 nm.

The molecular weight (i.e., the whole molecular weight of the agent) is considered a primary determinant in the pharmacokinetics, or in other words, how quickly it is cleared from the blood stream. The amount of labile (i.e., biologically available) iron is inversely correlated with the molecular weight of the iron-carbohydrate complex. Van Wyck (2004) J. Am. Soc. Nephrology 15, S107-S111, S109. That is to say, the magnitude of labile iron effect is greatest in iron-carbohydrate compounds of lowest molecular weight and least in those of the highest molecular weight. Generally, there is a direct relationship between the molecular weight of the agent and the mean diameter of the entire particle (i.e., the iron core along with the carbohydrate shell). In various embodiments, the mean diameter size of a particle of the iron carbohydrate complex is no greater than about 35 nm. For example, the particle mean size can be no greater than about 30 nm. As another example, the particle mean size can be no greater than about 25 nm. As another example, the particle mean size can be no greater than about 20 nm. As another example, the particle mean size can be no greater than about 15 nm. As a further example, the particle mean size can be no greater than about 10 nm. As another example, the particle mean size can be no greater than about 7 nm.

Absence of Significant Adverse Reaction to the Single Dosage Unit Administration Generally, a safe and effective amount of an iron carbohydrate complex is, for example, that amount that would cause the desired therapeutic effect in a patient while minimizing undesired side effects. The dosage regimen will be determined by skilled clinicians, based on factors such as the exact nature of the condition being treated, the severity of the condition, the age and general physical condition of the patient, and so on. Generally, treatment-emergent adverse events will occur in less than about 5% of treated patients. For example, treatment-emergent adverse events will occur in less than 4% or 3% of treated patients. Preferably, treatment-emergent adverse events will occur in less than about 2% of treated patients.

For example, minimized undesirable side effects can include those related to hypersensitivity reactions, sometimes classified as sudden onset closely related to the time of dosing, including hypotension, bronchospasm, layngospasm, angioedema or uticaria or several of these together. Hypersensitivity reactions are reported with all current intravenous iron products independent of dose. See generally Bailie et al. (2005) Nephrol Dial Transplant, 20(7), 1443-1449. As another example, minimized undesirable side effects can include those related to labile iron reactions, sometimes classified as nausea, vomiting, cramps, back pain, chest pain, and/or hypotension. Labile iron reactions are more common with iron sucrose, iron gluconate, and iron dextran when doses are large and given fast.

Pharmaceutical Formulations

In many cases, a single unit dose of iron carbohydrate complex may be delivered as a simple composition comprising the iron complex and the buffer in which it is dissolved. However, other products may be added, if desired, for example, to maximize iron delivery, preservation, or to optimize a particular method of delivery.

A "pharmaceutically acceptable carrier" includes any and all solvents, dispersion media, coatings, antibacterial and anti-fungal agents, isotonic and absorption delaying agents, and the like, compatible with pharmaceutical administration cit_bf(see e.g., Banker, Modern Pharmaceutics, Drugs and the Pharmaceutical Sciences, 4th ed. (2002) ISBN 0824706749; Remington The Science and Practice of Pharmacy, 21st ed. (2005) ISBN 0781746736). cit_af ref_bf (ref_num73)ref_afPreferred examples of such carriers or diluents include, but are not limited to, water, saline, Finger's solutions and dextrose solution. Supplementary active compounds can also be incorporated into the compositions. For intravenous administration, the iron carbohydrate complex is preferably diluted in normal saline to approximately 2-5 mg/ml. The volume of the pharmaceutical solution is based on the safe volume for the individual patient, as determined by a medical professional.

An iron complex composition of the invention for administration is formulated to be compatible with the intended route of administration, such as intravenous injection. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. Preparations can be enclosed in ampules, disposable syringes or multiple dose vials made of glass or plastic.

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, Cremophor EL™ (BASF; Parsippany, N.J.) or phosphate buffered saline (PBS). The composition must be sterile and should be fluid so as to be administered using a syringe. Such compositions should be stable during manufacture and storage and must be preserved against contamination from microorganisms, such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin.

Sterile injectable solutions can be prepared by incorporating an iron complex in the required amount in an appropriate solvent with a single or combination of ingredients as required, followed by sterilization. Methods of preparation of sterile solids for the preparation of sterile injectable solutions include vacuum drying and freeze-drying to yield a solid containing the iron complex and any other desired ingredient.

Active compounds may be prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

A single unit dose of iron carbohydrate complex may be intravenously administered in a volume of pharmaceutically acceptable carrier of, for example, about 1000 mg of elemental iron in about 200 ml to about 300 ml of diluent. For example, a single unit dose of iron carbohydrate complex may be intravenously administered in a volume of pharmaceutically acceptable carrier of about 1000 mg of elemental iron in about 250 ml of diluent. As another example, a single unit dose of iron carbohydrate complex may be intravenously administered in a volume of pharmaceutically acceptable carrier of about 1000 mg of elemental iron in about 215 ml of diluent.

A preferred pharmaceutical composition for use in the methods described herein contains VIT-45 as the active pharmaceutical ingredient (API) with about 28% weight to weight (m/m) of iron, equivalent to about 53% m/m iron (III)-hydroxide, about 37% m/m of ligand, ≤6% m/m of NaCl, and ≤10% m/m of water.

Kits for Pharmaceutical Compositions

Iron complex compositions can be included in a kit, container, pack or dispenser, together with instructions for administration according to the methods described herein. When the invention is supplied as a kit, the different components of the composition may be packaged in separate containers, such as ampules or vials, and admixed immediately before use. Such packaging of the components separately may permit long-term storage without losing the activity of the components. Kits may also include reagents in separate containers that facilitate the execution of a specific test, such as diagnostic tests.

The reagents included in kits can be supplied in containers of any sort such that the life of the different components are preserved and are not adsorbed or altered by the materials of the container. For example, sealed glass ampules or vials may contain lyophilized iron complex or buffer that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that, upon removal, permits the components to mix. Removable membranes may be glass, plastic, rubber, etc.

Kits may also be supplied with instructional materials. Instructions may be printed on paper or other substrate, and/or may be supplied on an electronic-readable medium, such as a floppy disc, CD-ROM, DVD-ROM, mini-disc, SACD, Zip disc, videotape, audio tape, etc. Detailed instructions may not be physically associated with the kit; instead, a user may be directed to an internet web site specified by the manufacturer or distributor of the kit, or supplied as electronic mail.

Having described the invention in detail, it will be apparent that modifications, variations, and equivalent embodiments are possible without departing the scope of the invention defined in the appended claims. It should be understood that all references cited are incorporated herein by reference. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Non-Toxicity Studies

Nonclinical toxicity of VIT-45 is very low, as is normal for Type I polynuclear iron (III)-hydroxide carbohydrate complexes. The single dose toxicity is so low that the $LD_{50}$ could not be estimated and is higher than 2000 mg iron/kg b.w. Mice tested with a single dose of 250 mg iron/kg b.w., injected within 2 seconds, showed no signs of illness. The highest non-lethal dose level of 1000 mg iron/kg b.w. in mice and rats is also very high in comparison to a single unit dose of, for example, 15 mg iron/kg b.w. once per week in humans. These results provide factors of about 70-fold a human dose, demonstrating a large safety margin for acute toxicity of the product.

Example 2

Pharmokinetic Studies

Pharmacokinetic and red blood cell measurements of $^{52}Fe/^{59}Fe$ labelled VIT-45 following i.v. administration using PET in 6 patients showed a red blood cell utilization from 61 to 99%. The 3 patients with iron deficiency anemia showed a utilization of radiolabelled iron of 91 to 99% after 24 days, compared to 61 to 84% for 3 patients with renal anemia. The terminal $t_{1/2}$ for VIT-45 was calculated to be approximately 16 hours, compared to about 6 hours for iron sucrose. In two further studies in patients with iron deficiency anemia, pharmacokinetic analyses revealed increases in exposure roughly proportional with VIT-45 dose (Cmax approximately 150 μg/mL and 320 μg/mL following 500 mg and 1000 mg doses, respectively). VIT-45 demonstrated a monoexponential elimination pattern with a $t_{1/2}$ in the range 7 to 18 hours. There was negligible renal elimination.

Example 3

Efficacy Studies

The main pharmacodynamic effects of VIT-45 were transient elevations of serum iron levels, TfS and serum ferritin. These effects were seen in all studies (where measured), following both single doses and repeated doses. The increase in serum ferritin levels illustrated the replenishment of the depleted iron stores, which is a well-identified and desired effect of iron therapy. In addition, transiently elevated TfS indicated that iron binding capacity was almost fully utilized following VIT-45 infusion.

Efficacy of iron replacement therapy is interpreted mainly in terms of the ability to normalise Hb levels and iron stores. In the multiple dose studies, patients demonstrated a slowly-developing, sustained increase in Hb levels during study participation. In one study, 37% and 48% of patients in Cohorts 1 and 2, respectively, had achieved normal Hb levels at the 4-week follow-up visit, and 75% and 73%, respectively, had achieved a ≥20 g/L increase in Hb on at least 1 occasion.

In another study (patients receiving regular haemodialysis), the majority of patients (61.7%) achieved an increase of Hb of ≥10 g/L at any point during the study. Serum ferritin and TfS levels showed a more prolonged elevation following repeated VIT-45 infusions, indicating a sustained replenishment of iron stores. However, elevated levels of ferritin and TfS indicating iron overload were avoided. In both of these studies, there was a gradual decrease in transferrin over time, also indicating successful iron replacement.

Example 4

Safety Assessments

Safety assessments were made in 73 patients with iron deficiency anemia (27 single-dose, 46 repeated-dose), and 166 patients with renal anemia (3 single-dose, 163 repeated-dose) who received VIT-45 at individual iron doses of 100 mg up to 1000 mg (cumulative doses of 100 to 2200 mg). These studies showed a safety profile equal to, or exceeding, currently available parenteral iron formulations.

In the single-dose studies, there were few adverse events and no serious adverse events or withdrawals due to adverse events. There were also no related clinically relevant adverse changes in vital signs, 12-lead ECGs or laboratory safety tests.

In the repeated-dose studies, there were no deaths attributed to VIT-45, while 10 patients experienced serious adverse events. All of these cases occurred in patients with renal anemia receiving haemodialysis and were considered not related to the VIT-45 treatment. Very few patients were withdrawn from the studies due to treatment-emergent adverse events, and only 2 withdrawals (due to allergic skin reactions) were considered possibly related to treatment. In each of the repeated-dose studies, no patients experienced clinically significant changes in 12-lead ECGs that were related to treatment. There were no consistent changes in laboratory safety parameters, although there was a low incidence (total 6 patients) of laboratory values reported as treatment-related treatment-emergent adverse events (elevated CRP, AST, ALT and GGT, abnormal liver function tests and elevated WBC).

Although many patients in these 2 studies had serum ferritin above 500 μg/L on at least 1 occasion during the study, very few patients also had TfS values >50%. Generally, the elevations of ferritin and TfS were of short duration. Iron overload was avoided using the dosing schedules defined in the studies.

Example 5

Integrated Safety Studies

The following example demonstrates the safety and effectiveness of parenteral VIT-45 in the treatment of anemia in a variety of patient populations, as determined from several integrated safety studies.

A total of 2429 subjects were treated with VIT-45 or control agents over 10 studies that provide safety data for VIT-45. Of these, 1709 subjects received VIT-45 (1095 in completed multicenter studies, 584 in placebo-controlled, single-dose, crossover studies and 30 in pharmacokinetic studies). The mean total dose of VIT-45 administered among the 1095 subjects in the completed multicenter studies was approximately 1300 mg; however, some subjects received VIT-45 doses as high as 3400 mg. The majority of the subjects treated were able to receive their calculated iron requirement in only 1 or 2 doses.

Table 2 provides a summary of VIT-45 studies described in this example.

Study A was a single-center, single-dose escalation, randomized, double-blind, placebo-controlled pharmacokinetic study. Subjects were male and female, between 18 and 45 years of age, inclusive, with mild iron-deficiency anemia. Treatment was a single IV bolus injection of VIT-45 at 100 mg, 500 mg, 800 mg, or 1000 mg. Examined pharmacokinetic parameters included total serum iron and pharmacodynamic (serum ferritin and transferrin, iron binding capacity, % TSATpost, hemoglobin, reticulocyte, and serum transferrin receptor concentrations) endpoints. Examined safety parameters included adverse events, clinical laboratory evaluations, vital signs, ECG, and physical examinations.

Study B was a single-center, single-dose, open label, uncontrolled pharmacokinetic study. Subjects were between 18 and 75 years of age with iron-deficiency or renal anemia with no other cause of anemia. Inclusion criteria included hemoglobin concentration between 9 and 13 g/dL, no blood transfusions in the previous 3 months, and no history of treatment with intravenous iron in the last 2 weeks. Treatment was a single IV bolus injection of VIT-45 at 100 mg labelled with $^{52}$Fe and $^{59}$Fe. Examined primary pharmacokinetic parameters included the distribution of $^{52}$Fe and incorporation of $^{59}$Fe into red blood cells. Examined safety parameters included adverse events, clinical laboratory evaluations, vital signs, and physical examinations.

Study C was an open-label, multicenter, randomized, multiple-dose, active-controlled postpartum anemia study. Subjects were female, postpartum within 10 days after delivery, with hemoglobin ≤10 g/dL at Baseline based on the average of 2 hemoglobin values drawn ≥18 hours postpartum. Treatment was once weekly doses of VIT-45 for six weeks. VIT-45 dosage was based on the calculated iron deficit (≤2500 mg total). Where screening serum transferrin saturation (TSAT) was ≤20% or screening ferritin was ≤50 ng/mL, dosage=pre-pregnancy weight (kg)×(15-baseline hemoglobin [g/dL])×2.4+500 mg. Where screening TSAT was >20% and screening ferritin was >50 ng/mL, dosage=pre-pregnancy weight (kg)×(15-baseline hemoglobin [g/dL])×2.4. Infusion of VIT-45 was as follows: ≤200 mg, administered as an undiluted intravenous push (IVP) over 1-2 minutes; 300-400 mg, administered in 100 cc normal saline solution (NSS) over 6 minutes; 500-1,000 mg administered in 250 cc NSS over 15 minutes. For primary efficacy, "success" was defined as an increase in hemoglobin of ≥2 g/dL anytime between baseline and end of study or time of intervention, while "failure" was defined as <2 g/dL increase in hemoglobin at all times between baseline and end of study or time of intervention. Examined safety parameters included adverse events, clinical laboratory evaluations, vital signs, and physical examinations.

Study D was a multicenter, open-label, randomized, active-controlled, multiple-dose postpartum anemia study. Subjects were adult women ≥18 years old with postpartum anemia within 6 days after delivery. Treatment was administered once-weekly for a maximum of 3 infusions. Patients received IV infusions of 16.7 mL/min to deliver a maximum dose of 1000 mg iron per infusion. Patients received VIT-45 infusions once weekly for up to 3 occasions until the calculated cumulative dose was reached. Patients ≤66 kg received a minimum dose of 200 mg and a maximum dose of 15 mg iron/kg during each infusion. Patients >66 kg received a dose of 1000 mg on the first dosing occasion, and a minimum dose of 200 mg and a maximum dose of 1000 mg at each subsequent dosing. Doses of 200-400 mg were diluted in 100 cc NSS and 500-1000 mg were diluted in 250 cc NSS. Primary efficacy was examined as change from baseline levels of hemoglobin to Week 12. Examined safety parameters included adverse events in the mother and breast-fed infant, adverse events leading to discontinuation of treatment, vital signs, 12-lead electrocardiogram (ECG), physical examinations, and clinical laboratory panels.

Study E was a multicenter, open-label, randomized, active-controlled, multiple-dose hemodialysis-associated anemia study. Subjects were adult male or female subjects between the ages of 18 and 80 years (inclusive) requiring haemodialysis with iron deficiency secondary to chronic renal failure. Dosing started on Day 1, Week 0 for both treatment arms and continued 2 or 3 times weekly until the individual calculated cumulative dose was reached. Patients received 200 mg VIT-45 during their scheduled haemodialysis sessions (2-3 sessions/week) until the calculated cumulative dose was reached. Cumulative total iron requirement was calculated for each patient using the Ganzoni formula. Primary Efficacy was examined as the percentage of patients reaching an increase in hemoglobin ≥10 g/L at 4 weeks after baseline. Examined safety parameters included adverse events, vital signs, 12-lead ECG, physical examinations, and clinical laboratory evaluations.

Study F was a multicenter, open-label, multiple dose, uncontrolled hemodialysis-associated anemia study. Subjects were male and female patients 18-65 years of age, inclusive, with haemodialysis-associated anemia undergoing maintenance haemodialysis. Treatment duration was a maximum of six weeks. Patients received 200 mg VIT-45 during their scheduled haemodialysis sessions (2-3 sessions/week) until the calculated cumulative dose was reached. Cumulative total iron requirement was calculated for each patient using the Ganzoni formula. Efficacy was examined as correction of iron deficiency and hemoglobin concentration of the patient. Examined safety parameters included adverse events, vital signs, 12-lead ECG, physical examinations, hematology and blood chemistry profiles, and urea reduction ratio.

Study G was a multicenter, multiple-dose open-label, uncontrolled gastrointestinal disorder-associated anemia study. Subjects were males and females between 18 and 60 years of age, inclusive, with moderate stable iron-deficiency anemia secondary to a gastrointestinal disorder and a calculated total iron requirement ≥1000 mg; ≥50% of patients in each cohort were to require ≥1500 mg total iron. Duration of treatment was single doses at weekly intervals for up to 4 weeks (Cohort 1) or 2 weeks (Cohort 2). Administration of VIT-45 was by IV bolus injection of 500 mg (Cohort 1) or 1000 mg (Cohort 2), where total iron requirement for each patient, which determined how many weekly infusions were received, was calculated using the formula of Ganzoni. Examined pharmacokinetic parameters included total serum iron and pharmacodynamic (hemoglobin, ferritin, TSAT) endpoints. Examined safety parameters included adverse events, clinical laboratory evaluations, vital signs, ECG, physical examinations, and elevated serum ferritin (>500 µg/L) AND elevated TSAT (>45%).

Study H was a multicenter, multiple-dose randomized, open-label, active-controlled gastrointestinal disorder-associated anemia study. Subjects were males and females aged 18 to 80 years, inclusive, with iron-deficiency anemia secondary to chronic inflammatory bowel disease (ulcerative colitis or Crohn's disease) and a calculated total iron requirement of at least 1000 mg total iron. Treatment was weekly VIT-45 infusions, with a maximum of 3 infusions permitted in a single treatment cycle. Administration consisted of an infusion on Day 1, with subsequent infusions at weekly intervals up to a maximum of 1000 mg iron per dose. The doses were continued until the patient received the cumulative dose based on their individual requirement for iron. Primary efficacy was examined as change from baseline to Week 12 in hemoglobin. Examined safety parameters included adverse events, vital signs, 12-lead ECG, physical examinations, and clinical laboratory evaluations.

Study I was an open label, multiple-dose, multicenter, randomized, active-control anemia due to heavy uterine bleeding study. Subjects were females at least 18 years of age with iron-deficiency anemia secondary to heavy uterine bleeding. Duration of treatment was six weeks. VIT-45 dosage was based on the calculated iron deficit as follows: where baseline TSAT ≤20% or baseline ferritin ≤50 ng/mL, VIT-45 total dose in mg=baseline weight (kg)×(15-baseline hemoglobin [g/dL])×2.4+500; where baseline TSAT >20% and baseline ferritin >50 ng/mL, VIT-45 total dose in mg=baseline weight (kg)×(15-baseline hemoglobin [g/dL])×2.4. For administration, ≤200 mg was administered as an undiluted IVP over 1-2 minutes; 300-400 mg was administered in 100 cc NSS over 6 minutes; and 500-1,000 mg was administered in 250 cc NSS over 15 minutes. Primary efficacy was examined as the proportion of subjects achieving success, defined as an increase in hemoglobin of ≥2.0 g/dL anytime between baseline and end of study or time of intervention. Examined safety parameters included adverse events, clinical laboratory evaluations, vital signs, and physical examinations.

Study J was a multicenter, single-dose blinded, randomized, placebo-controlled crossover iron deficiency anemia study. Subjects were male or female, at least 18 years of age, with a hemoglobin ≤12 g/dL, TSAT ≤25%, and ferritin <300 ng/mL (iron-deficiency anemia due to dialysis or non-dialysis dependent chronic kidney disease or inflammatory bowel disease), or ferritin ≤100 ng/mL (iron-deficiency anemia due to other conditions). Treatment was two single doses seven days apart. Administration of VIT-45 occurred over 15 minutes and was ≤1000 mg (15 mg/kg for weight ≤66 kg). For pharmacokinetic variables, total serum iron was assessed using Atomic Absorption methodology. Examined safety parameters included adverse events, clinical laboratory evaluations, vital signs, and physical examinations.

TABLE 2

| | | Summary of Safety Studies of VIT-45 | |
|---|---|---|---|
| Study Number | Subjects | Intravenous Dose(s) of VIT-45 | Comparator |
| | | Pharmacokinetic Studies | |
| A | Total: 32<br>VIT-45: 24 | Single doses of:<br>100 mg via bolus injection<br>500 mg, 800 mg, 1000 mg diluted in 250 mL of<br>NSS administered by IV infusion over 15 minutes | Placebo |
| B | Total: 6<br>VIT-45: 6 | Single dose of 100 mg labelled with $^{52}$Fe and $^{59}$Fe administered as an IV injection over 10 minutes | None |
| | | Studies in Subjects with Postpartum Anemia | |
| C | Total: 352<br>VIT-45: 174 | Cumulative total iron requirement was calculated for each patient. Patients received IV infusions to deliver a maximum dose of 1000 mg iron per infusion. Patients received VIT-45 infusions once weekly until the calculated cumulative dose was reached or a maximum of 2500 mg had been administered. Doses ≤200 mg were administered IV push over 1-2 minutes; doses of 300-400 mg were diluted in 100 cc NSS and administered over 6 minutes; doses of 500-1000 mg were diluted in 250 cc NSS and administered over 15 minutes. | Oral iron (ferrous sulfate) 325 mg TID for 6 weeks |
| D | Total: 344<br>VIT-45: 227 | Cumulative total iron requirement was calculated for each patient using the Ganzoni formula. | Oral iron (ferrous sulfate) 100 mg BID for 12 weeks |
| | | Studies in Subjects Undergoing Hemodialysis | |
| E | Total: 237<br>VIT-45: 119 | Patients received 200 mg IV bolus injection of study drug during their scheduled hemodialysis sessions (2-3 sessions/week) until the calculated cumulative dose was reached. Cumulative total iron requirement was calculated for each patient using the Ganzoni formula. | Venofer ®; patients received 200 mg IV injection over 10 minutes of study drug during their scheduled hemodialysis sessions (2-3 sessions/week) until the calculated cumulative dose was reached. Cumulative total iron requirement was calculated for each patient using the Ganzoni formula.[a] |
| F | Total: 163<br>VIT-45: 162 | Patients received 200 mg IV push of study drug during their scheduled hemodialysis sessions (2-3 sessions/week) until the calculated cumulative dose was reached. Cumulative total iron requirement was calculated for each patient using the Ganzoni formula. | None |
| | | Studies in Subjects with Gastrointestinal Disorders | |
| G | Total: 46<br>VIT-45: 46 | 500 mg or 1000 mg iron by IV infusion at weekly intervals for up to 4 weeks (500 mg) or 2 weeks (1000 mg); maximum total dose of 2000 mg. The last dose could have been less, depending on the calculated total iron requirement. Doses were diluted in 250 cc NSS and administered by IV infusion over 15 minutes. | None |
| H | Total: 200<br>VIT-45: 137 | Cumulative total iron requirement was calculated for each patient using the Ganzoni formula. | Oral iron (ferrous sulfate) 100 mg BID for 12 weeks |
| | | Study in Subjects with Heavy Uterine Bleeding | |
| I | Total: 456<br>VIT-45: 230 | ≤1000 mg/week (15 mg/kg for weight ≤66 kg); patients received VIT-45 infusions once weekly until the calculated cumulative dose was reached or a maximum of 2500 mg had been administered. Doses ≤200 mg were administered IV push over 1-2 minutes; doses of 300-400 mg were diluted in 100 cc NSS and administered over 6 minutes; doses of 500-1000 mg were diluted in 250 cc NSS and administered over 15 minutes. | Oral iron (ferrous sulfate) 325 mg TID for 6 weeks |
| | | Study in Subjects with Iron Deficiency Anemia | |
| J | Total: 594<br>VIT-45: 584 | Single dose of ≤1000 mg by IV infusion over 15 minutes (15 mg/kg for weight ≤66 kg). Doses | Placebo |

TABLE 2-continued

Summary of Safety Studies of VIT-45

| Study Number | Subjects | Intravenous Dose(s) of VIT-45 | Comparator |
|---|---|---|---|
| | | ≤500 mg were diluted in 100 cc NSS and doses of >500-1000 mg were diluted in 250 cc NSS. Pharmacokinetic subjects: single 1,000 mg dose by IV infusion | |

The majority of the subjects who received VIT-45 completed the study. The incidence of premature discontinuations in the completed multicenter studies was 10% in the VIT-45 group which is comparable to that observed in the oral iron (9.6%) and Venofer (13.6%) groups. Reasons for premature discontinuation were generally comparable among the treatment groups, except that the incidence of adverse events leading to discontinuation were higher in the Venofer group (5.9%) compared to the VIT-45 (1.8%) and oral iron (2.1%) groups, demonstrating the overall tolerability of VIT-45.

The overall incidences of treatment-emergent adverse events were comparable between the VIT-45 (49.5%) and oral iron (51.2%) groups in the completed multicenter studies; the incidence in the Venofer group was lower (39.0%); however, the number of subjects in the VIT-45 group is almost 10-fold that of the Venofer group. Treatment-emergent adverse events experienced by ≥2% of the 1095 VIT-45 subjects included headache (8.6%), abdominal pain (2.5%), nausea (2.4%), blood phosphate decreased (2.4%), hypertension (2.2%), nasopharyngitis (2.0%), and hypotension (2.0%). As expected, the most notable difference between subjects treated with VIT-45 and those treated with oral iron was for the incidence of gastrointestinal events (31.0% vs. 12.8%), specifically the incidences of constipation, diarrhea, nausea, and vomiting, which were more than double that observed in the VIT-45 group.

In the calculated dose/first-dose 1,000 mg studies, no statistically significant difference was observed between the VIT-45 (49.5%) and oral iron (51.2%) groups for the overall incidence of treatment-emergent adverse events. The incidence of gastrointestinal disorders was statistically significantly (p<0.0001) higher in the oral iron group (31.0%) compared to the VIT-45 group (15.2%), while the incidences of adverse events associated with investigations and skin and subcutaneous tissue disorders were statistically significantly higher in the VIT-45 group (9.1% and 7.3%, respectively) compared to the oral iron group (3.9% and 2.4%, respectively). Among the gastrointestinal disorders, greater proportions of subjects in the oral iron group than the VIT-45 group experienced constipation, nausea, diarrhea, and vomiting, while a greater proportion of VIT-45 subjects experienced abdominal pain than oral iron subjects. Among the adverse events associated with investigations, greater proportions of VIT-45 subjects experienced blood phosphate decreased and GGT increased than oral iron subjects. Among the adverse events associated with skin and subcutaneous tissue disorders, greater proportions of VIT-45 subjects experienced rash and pruritus than oral iron subjects.

The only drug-related treatment-emergent adverse events reported by at least 2% of VIT-45 subjects in the calculated dose/first-dose 1,000 mg studies were headache (3.9%) and blood phosphate decreased (3.3%). The incidence of treatment-emergent adverse events reported on the first day of dosing in the calculated dose/first-dose 1,000 mg studies was statistically significant higher in the VIT-45 group compared to the oral iron group (6.8% vs. 2.7%). On the first day of dosing, the VIT-45 group had statistically significantly greater proportions of subjects who experienced general disorders and administration site conditions, primarily events associated with the site of study drug infusion, and skin and subcutaneous tissue disorders, primarily rash and urticaria, compared to the oral iron group.

The overall incidence of treatment-emergent adverse events was similar among VIT-45 subjects treated with either the 200 mg or 1000 mg doses. The only notable difference was for the higher incidence of headache in the 1000-mg group, which was almost double that observed for the 200-mg group. No meaningful trends were apparent with respect to the incidence of treatment-emergent adverse events when analyzed by gender, age, race, weight, or etiology of anemia.

There were no deaths in the study attributed to VIT-45. The incidence of other serious adverse events among VIT-45 subjects was low (3% in all completed multicenter studies and 0.3% in the placebo-controlled, single-dose crossover study) and none were considered related to study drug. The incidence of premature discontinuation due to adverse events was comparable between the VIT-45 group (2.1%) and the other active treatment groups (3.1% oral iron and 2.5% Venofer). The incidence of drug-related treatment-emergent adverse events of hypersensitivity was 0.2%, the same as that observed with oral iron (0.2%). Drug-related mild or moderate hypotension was observed in 4 (0.2%) VIT-45 subjects, none of which were considered serious, led to premature discontinuation, or were symptomatic. Treatment-emergent adverse events indicative of potential allergic reactions including rash, pruritus, and urticaria were reported by <2% of subjects who were treated with VIT-45; none of these events was considered serious and few led to premature discontinuation.

Laboratory evaluations of mean changes from baseline and potentially clinically significant values demonstrated no clinically meaningful changes for the majority of the parameters evaluated. However, during the conduct of the latter portion of the clinical program, transient, asymptomatic decreases in blood phosphate levels were observed among subjects treated with VIT-45. The decreases were apparent approximately 7 days after the initial dose of VIT-45 and the median time to recovery was approximately 2 weeks. No subjects reported an adverse event that was related to serum phosphate and no subject discontinued from the study due to decreased serum phosphate. The only predictor of change in serum phosphate was that subjects with higher baseline serum phosphate values had larger decreases in serum phosphate. The fact that the majority of oral iron-treated subjects also had a post-baseline decrease in phosphate and the negative correlation of baseline serum phosphate with changes in serum phosphate for both the VIT-45 and oral iron treatment groups suggest that the mechanism is intrinsic to iron therapy in this severely anemic population.

Overall, no clinically meaningful changes in vitals signs evaluations were associated with VIT-45 administration.

Safety data from more than 1700 subjects demonstrate the safety and tolerability of VIT-45.

What is claimed is:

1. A method of treating a disease, disorder, or condition characterized by iron deficiency or dysfunctional iron metabolism resulting in reduced bioavailability of dietary iron, comprising administering to a subject in need thereof an iron carbohydrate complex in a single dosage unit of at least 0.7 grams of elemental iron, wherein:
   the iron carbohydrate complex is substantially non-immunogenic, and has substantially no cross reactivity with anti-dextran antibodies; and
   the iron carbohydrate complex is an iron polyisomaltose complex.

2. The method of claim 1, wherein the disease, disorder, or condition comprises anemia.

3. The method of claim 2, wherein the anemia comprises iron deficiency anemia.

4. The method of claim 2, wherein:
   (i) the anemia comprises an iron deficiency anemia associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; chronic ingestion of alcohol; chronic ingestion of salicylates; chronic ingestion of steroids; chronic ingestion of non-steroidal anti-inflammatory agents; or chronic ingestion of erythropoiesis stimulating agents; or
   (ii) the anemia is of a chronic disease selected from among rheumatoid arthritis; cancer; Hodgkin's leukemia; non-Hodgkin's leukemia; cancer chemotherapy; inflammatory bowel disease; ulcerative colitis thyroiditis; hepatitis; systemic lupus erythematosus; polymyalgia rheumatica; sclerodema; mixed connective tissue disease; Sjogren's syndrome; congestive heart failure/cardiomyopathy; and idiopathic geriatric anemia; or
   (iii) the anemia is due to impaired iron absorption or poor nutrition; or
   (iv) the anemia is associated with Crohn's Disease; gastric surgery; ingestion of drug products that inhibit iron absorption; or chronic use of calcium.

5. The method of claim 1, wherein the disease, disorder, or condition is selected from among restless leg syndrome; blood donation; hair loss; and attention deficit disorder.

6. The method of claim 1, wherein the single dosage unit of elemental iron is at least about 1.0 grams.

7. The method of claim 1, wherein the single dosage unit of elemental iron is at least about 1.5 grams.

8. The method of claim 1, wherein the single dosage unit of elemental iron is at least about 2.0 grams.

9. The method of claim 1, wherein the single dosage unit of elemental iron is administered in about 15 minutes or less.

10. The method of claim 1, wherein the single dosage unit of elemental iron is administered in about 5 minutes or less.

11. The method of claim 1, wherein:
    mean iron core size is at least about 1 nm but no greater than about 9 nm; or
    mean size of a particle of the iron carbohydrate complex is no greater than about 35 nm.

12. The method of claim 1, wherein the iron carbohydrate complex is administered parenterally.

13. The method of claim 12, wherein:
    (i) parenteral administration comprises intravenous infusion and the single unit dose of iron carbohydrate complex is administered at a concentration of about 1000 mg elemental iron in about 200 ml to about 300 ml of diluent; or
    (ii) parenteral administration comprises bolus injection and the single unit dose of iron carbohydrate complex is administered at a concentration of about 1000 mg elemental iron in about 200 ml to about 300 ml of diluent; or
    (iii) parenteral administration comprises intramuscular injection and the single unit dose of iron carbohydrate complex is administered at a concentration of about 500 mg elemental iron in less than about 10 ml diluent.

14. The method of claim 1, further comprising a second administration of said iron carbohydrate complex upon recurrence of at least one symptom of the disease, disorder, or condition.

15. The method of claim 1, wherein the subject does not experience a significant adverse reaction.

16. The method of claim 1, wherein the iron carbohydrate complex has a pH between about 5.0 to about 7.0; physiological osmolarity; an iron core size no greater than about 9 nm; a mean diameter particle size no greater than about 35 nm; and a blood half-life of between about 10 hours to about 20 hours.

17. The method of claim 1, wherein the iron carbohydrate complex contains about 24% to about 32% w/w elemental iron; contains about 25% to about 50% w/w carbohydrate; and has a molecular weight of about 90,000 daltons to about 800,000 daltons.

18. The method of claim 1, wherein the single dosage unit of elemental iron is administered in about 2 minutes or less.

19. The method of claim 1, wherein the single dosage unit of elemental iron is at least about 0.8 grams.

20. The method of claim 1, wherein the single dosage unit of elemental iron is at least about 0.9 grams.

21. The method of claim 1, wherein:
    (i) the iron deficiency comprises iron deficiency with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; chronic ingestion of alcohol; chronic ingestion of salicylates; chronic ingestion of steroids; chronic ingestion of non-steroidal anti-inflammatory agents; or chronic ingestion of erythropoiesis stimulating agents; or
    (ii) the iron deficiency is of a chronic disease selected from among rheumatoid arthritis; cancer; Hodgkin's leukemia; non-Hodgkin's leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sjorgen's syndrome; congestive heart failure/cardiomyopathy; and idiopathic geriatric anemia; or
    (iii) the iron deficiency is due to impaired iron absorption or poor nutrition; or (iv) the iron deficiency is associated with Crohn's Disease; gastric surgery; ingestion of drug products that inhibit iron absorption; or chronic use of calcium.

22. The method of claim 1, wherein the polyisomaltose is reduced polyisomaltose.

\* \* \* \* \*